United States Patent [19]

Call et al.

[11] Patent Number: 5,726,288
[45] Date of Patent: Mar. 10, 1998

[54] LOCALIZATION AND CHARACTERIZATION OF THE WILMS' TUMOR GENE

[75] Inventors: Katherine M. Call, Malden; Thomas M. Glaser, Belmont, both of Mass.; Caryn Y. Ito, Chapel Hill, N.C.; Alan J. Buckler, Cambridge, Mass.; Jerry Pelletier, Montreal, Canada; Daniel A. Haber, Cambridge, Mass.; Elise A. Rose, Oakland, Calif.; David E. Housman, Newton, Mass.; Wendy Bruening, Montreal; Andre Darveau, St. Foy, both of Canada

[73] Assignee: Massachusetts Institute of Technology, Cambridge, Mass.

[21] Appl. No.: 102,942

[22] Filed: Aug. 2, 1993

Related U.S. Application Data

[63] Continuation-in-part of Ser. No. 614,161, Nov. 13, 1990, abandoned, which is a continuation-in-part of Ser. No. 435,780, Nov. 13, 1989, abandoned.

[51] Int. Cl.$^6$ .................................................. C07K 14/435
[52] U.S. Cl. ............................................................ 530/350
[58] Field of Search .............................. 530/350; 536/23.5

[56] References Cited

FOREIGN PATENT DOCUMENTS

PCT/UA90/06629  11/1990  WIPO.

OTHER PUBLICATIONS

Call, K. et al., "Isolation and Mapping of Cosmid Clones and Isolation of a Candidate Gene for WILMS Tumor" 51:974 (1989) (From *Cytogenics & Cell Genetics—Human Gene Mapping #10, New Haven Conference*, Abstract No. A2310).

Glaser, T. et al., "The Ultrafine Structure of the WAGR Gene Complex" 51:1005 (1989) (From *Cytogenics & Cell Genetics—Human Gene Mapping #10, New Haven Conference*, Abstract No. A2331).

Lichter, P. et al., "Mapping of Cosmid DNAs on Human Chromosome 11 by in Situ Hybridization" 51:1033 (1989) (From *Cytogenics & Cell Genetics—Human Gene Mapping #10, New Haven Conference*, Abstract No. A2176).

Rose, E.A. et al., "A Complete Physical Map of the WAGR Region Using Irradiation Reduced Hybrids, and Assessment of a Candidate Wilms' Tumor Gene" 51:1068 (1989) (From *Cytogenics & Cell Genetics—Human Gene Mapping #10, New Haven Conference*, Abstract No. A2359).

Call, K.M. et al., "Isolation of a cDNA in the WAGR Region: A Candidate Gene for Wilms' Tumor" *The American Journal of Human Genetics*, 45(4) (1989) (From *1989 Annual Meeting of the American Society of Human Genetics*, Abstract No. 0700 2.9).

Haber, D.A., et al., "An Internal Deletion within an 11p13 Zinc Finger Gene Contributes to the Development of Wilms' Tumor," *Cell*, 61:1257–1269 (1990).

Buckler, A.J., et al., "Isolation, Characterization, and Expression of the Murine Wilms' Tumor Gene (WT1) During Kidney Development," *Mol. & Cell. Biol.*, 11(3):1707–1712 (1991).

Pelletier, J., et al., "WT1 Mutations Contribute to Abnormal Genital System Development and Hereditary Wilms' Tumour," *Nature*, 353:431–434 (1991).

Pelletier, J., et al., "Germline Mutations in the Wilms' Tumor Suppressor Gene Are Associated with Abnormal Urogenital Development in Denys–Drash Syndrome," *Cell*, 67:437–447 (1991).

Bruening, W., et al., "Germline Intronic and Exonic Mutations in the Wilms' Tumour Gene (WT1) Affecting Urogenital Development," *Nature Genetics*, 1:144–148 (1992).

Bruening, W., et al., "Analysis of the 11p13 Wilms' Tumor Suppressor Gene (WT1) in Ovarian Tumors," *Cancer Investigation*, 11(4):393–399 (1993).

Gessler, M., et al., "Homozygous Deletion in Wilms Tumours of a Zinc–Finger Gene Identified by Chromosome Jumping," *Nature*, 343:774–778 (1990).

Gessler, M., et al., "Molecular Mapping and Cloning of the Breakpoints of a Chromosome 11p14.1-p13 Deletion Associated with the AGR Syndrome," *Genomics*, 3(2):117–123 (1988).

Call, K.M., et al., "Isolation and Characterization of a Zinc Finger Polypeptide Gene at the Human Chromosome 11 Wilms' Tumor Locus," *Cell*, 60:509–520 (1990).

Pelletier, J., et al., "Expression of the Wilms' Tumor Gene WT1 in the Murine Urogenital System," *Genes & Dev.*, 5:1345–1356 (1991).

Compton, D.A., et al., "Long Range Physical Map of the Wilms' Tumor–Aniridia Region on Human Chromosome 11," *Cell*, 55:827–836 (1988).

Lewis, W.H., et al., "Homozygous Deletion of a DNA Marker from Chromosome 11p13 in Sporadic Wilms Tumor," *Genomics*, 3:25–31 (1988).

Porteous, D.J., et al., "HRAS1-Selected Chromosome Transfer Generates Markers that Colocalize Aniridia–and Genitourinary Dysplasia–Associated Translocation Breakpoints and the Wilms Tumor Gene Within Band 11p13," *Proc. Natl. Acad. Sci. USA*, 84:5355–5359 (1987).

(List continued on next page.)

*Primary Examiner*—Robert A. Wax
*Assistant Examiner*—Kawai Lau
*Attorney, Agent, or Firm*—Hamilton, Brook, Smith & Reynolds, P.C.

[57] ABSTRACT

The Wilms' tumor gene associated with 11p3 locus on the human chromosome, as well as a method of analyzing cells for the gene is described and characterized. The gene encodes a transcription unit approximately 50 kb in size and a mRNA of approximately 3 kb, which is expressed in predominantly in kidney and gonadal tissue. The gene is alternative spliced producing four very similar mRNA transcripts. The polypeptides encoded by the Wilms' tumor DNA includes four "zinc fingers" and a region rich in proline and glutamine, suggesting that the polypeptide has a role in transcription regulation.

5 Claims, 19 Drawing Sheets

OTHER PUBLICATIONS

Gessler, M., et al., "Cloning of Breakpoints of a Chromosome Translocation Identifies the AN2 Locus," *Science*, 244:1575–1578 (1989).

Glaser, T., et al., "The β–Subunit of Follicle–Stimulating Hormone is Deleted in Patients With Aniridia and Wilms' Tumour, Allowing a Further Definition of the WAGR Locus," *Nature*, 321(6073):882–887 (1986).

Davis, L.M., et al., "Two Anonymous DNA Segments Distinguish the Wilms' Tumor and Aniridia Loci," *Science*, 241:840–842 (1988).

Francke, U., et al., "Aniridia–Wilms' Tumor Association: Evidence for Specific Deletion of 11p13," *Cytogenet. Cell Genet.*, 24:185–192 (1979).

Francke U., "A Gene for Wilms Tumour?" *Nature*, 343:692–694 (1990).

Koufos, A., et al., "Familial Wiedemann–Beckwith Syndrome and a Second Wilms Tumor Locus Both Map to 11p15.5," *Am. J. Hum. Genet.*, 44:711–719 (1989).

Matsunaga, E., "Genetics of Wilms' Tumor," *Hum Genet.*, 57:231–246 (1981).

Riccardi, V.M., et al., "Chromosomal Imbalance in the Aniridia–Wilms' Tumor Association: 11p Interstitial Deletion," *Pediatrics*, 61(4):604–610 (1978).

Lavendan, C., et al., "Molecular Definition of de novo and Genetically Transmitted WAGR–Associated Rearrangements of 11p13," *Cytogenet. Cell Genet.*, 50:70–74 (1989).

Yunis, J.J., et al., "Familial Occurrence of the Aniridia–Wilms Tumor Syndrome with Deletion 11p13–14.1," *The J. of Pediatrics*, 96(6):1027–1030 (1980).

Kolata, G.B., "Genes and Cancer: The Story of Wilms Tumor," *Science*, 207:970–971 (1980).

Hoffman, M., "One Wilms' Tumor Gene Is Cloned; Are There More?, " *Science*, 246(4936) (1989).

Junien, C., et al., "Catalase Determination in Various Etiologic Forms of Wilms' Tumor and Gonadoblastoma," *Cancer Genetics and Cytogenetics*, 10(1):51–57 (1983).

Huff, V., et al., "Evidence for WT1 as a Wilms' Tumor (WT) Gene: Intragenic Germinal Deletion in Bilateral WT," *Am. J. Hum. Genet.*, 48:997–1003 (1991).

Turleau, C., et al., "Del11p13/Nephroblastoma Without Aniridia," *Hum. Genet.*, 67:455–456 (1984).

Knudson, Jr., A.G., et al., "Mutation and Cancer: A Model for Wilms' Tumor of the Kidney," *J. of the Natl. Cancer Instit.*, 48(2):313–324 (1972).

Knudson, Jr., A.G., "Mutation and Cancer: Statistical Study of Retinoblastoma," *Proc. Natl. Acad. Sci USA*, 68(4):820–823 (1971).

Vogel, F., "Genetics of Retinoblastoma," *Hum. Genet.*, 52:1–16 (1979).

Matsunaga, E., "Retinoblastoma: Host Resistance and Age at Onset," *JncI.*, 63(4):933–939 (1979).

Lee, W–H., et al., "Human Retinoblastoma Susceptibility Gene: Cloning, Identification, and Sequence," *Science*, 235:1394–1398 (1987).

Friend, S.H., et al., "A Human DNA Segment with Properties of the Gene That Predisposes to Retinoblastoma and Osteosarcoma," *Nature*, 323:643–646 (1986).

Cavenee, W.K., et al., "Expression of recessive alleles by Chromosomal Mechanisms in Retinoblastoma," *Nature*, 305 (1983).

```
   1  GAGGAGCAGTGCCTGAGCGCCTTCACTGTCCACTTTTCCGGCCAGTTCACTGGCACAGCC
   1   E  E  Q  C  L  S  A  F  T  V  H  F  S  G  Q  F  T  G  T  A
  61  GGAGCCTGTCGCTACGGGCCCTTCGGTCCTCCTCCGCCCAGCCAGGCGTCATCCGGCCAG
  21   G  A  C  R  Y  G  P  F  G  P  P  P  P  S  Q  A  S  S  G  Q
 121  GCCAGGATGTTTCCTAACGCGCCCTACCTGCCCAGCTGCCTCGAGAGCCAGCCCGCTATT
  41   A  R  M  F  P  N  A  P  Y  L  P  S  C  L  E  S  Q  P  A  I
 181  CGCAATCAGGGTTACAGCACGGTCACCTTCGACGGGACGCCCAGCTACGGTCACACGCCC
  61   R  N  Q  G  Y  S  T  V  T  F  D  G  T  P  S  Y  G  H  T  P
 241  TCGCACCATGCGGCGCAGTTCCCCAACCACTCATTCAAGCATGAGGATCCCATGGGCCAG
  81   S  H  H  A  A  Q  F  P  N  H  S  F  K  H  E  D  P  M  G  Q
 301  CAGGGCTCGCTGGGTGAGCAGCAGTACTCGGTGCCGCCCCCGGTCTATGGCTGCCACACC
 101   Q  G  S  L  G  E  Q  Q  Y  S  V  P  P  P  V  Y  G  C  H  T
 361  CCCACCGACAGCTGCACCGGCAGCCAGGCTTTGCTGCTGAGGACGCCCTACAGCAGTGAC
 121   P  T  D  S  C  T  G  S  Q  A  L  L  L  R  T  P  Y  S  S  D
 421  AATTTATACCAAATGACATCCCAGCTTGAATGCATGACCTGGAATCAGATGAACTTAGGA
 141   N  L  Y  Q  M  T  S  Q  L  E  C  M  T  W  N  Q  M  N  L  G
 481  GCCACCTTAAAGGGCCACAGCACAGGGTACGAGAGCGATAACCACACAACGCCCATCCTC
 161   A  T  L  K  G  H  S  T  G  Y  E  S  D  N  H  T  T  P  I  L
 541  TGCGGAGCCCAATACAGAATACACACGCACGGTGTCTTCAGAGGCATTCAGGATGTGCGA
 181   C  G  A  Q  Y  R  I  H  T  H  G  V  F  R  G  I  Q  D  V  R
 601  CGTGTGCCTGGAGTAGCCCCGACTCTTGTACGGTCGGCATCTGAGACCAGTGAGAAACGC
 201   R  V  P  G  V  A  P  T  L  V  R  S  A  S  E  T  S  E  K  R
 661  CCCTTCATGTGTGCTTACCCAGGCTGCAATAAGAGATATTTTAAGCTGTCCCACTTACAG
 221   P  F  M  C  A  Y  P  G  C  N  K  R  Y  F  K  L  S  H  L  Q
 721  ATGCACAGCAGGAAGCACACTGGTGAGAAACCATACCAGTGTGACTTCAAGGACTGTGAA
 241   M  H  S  R  K  H  T  G  E  K  P  Y  Q  C  D  F  K  D  C  E
 781  CGAAGGTTTTTTCGTTCAGACCAGCTCAAAAGACACCAAAGGAGACATACAGGTGTGAAA
 261   R  R  F  F  R  S  D  Q  L  K  R  H  Q  R  R  H  T  G  V  K
 841  CCATTCCAGTGTAAAACTTGTCAGCGAAAGTTCTCCCGGTCCGACCACCTGAAGACCCAC
 281   P  F  Q  C  L  T  C  Q  R  K  F  S  R  S  N  H  L  K  T  H
 901  ACCAGGACTCATACAGGTGAAAAGCCCTTCAGCTGTCGGTGGCCAAGTTGTCAGAAAAAG
 301   T  R  T  H  T  G  Q  K  P  F  S  C  R  W  P  S  C  Q  K  K
 961  TTTGCCCGGTCAGATGAATTAGTCCGCCATCACAACATGCATCAGAGAAACATGACCAAA
 321   F  A  R  S  D  E  L  V  R  H  H  N  M  H  Q  R  N  M  T  K
1021  CTCCAGCTGGCGCTTTGAGGGGTCTCCCTCGGGGACCGTTCAGTGTCCCAGGCAGCACAG
 641   L  Q  L  A  L
1081  TGTGTGAACTGCTTTCAAGTCTGACTCTCCACTCCTCCTCACTAAAAAGGAAACTTCAGT
1141  TGATCTTCTTCATCCAACTTCCAAGACAAGATACCGGTGCTTCTGGAAACTACCAGGTGT
1201  GCCTGGAAGAGTTGGTCTCTGCCCTGCCTACTTTTAGTTGACTCACAGGCCCTGGAGAAG
1261  CAGCTAACAATGTCTGGTTAGTTAAAAGCCCATTGCCATTTGGTGTGGATTTTCTACTGT
1321  AAGAAGAGCCATAGCTGATCATGTCCCCCTGACCCTTCCCTTCTTTTTTTATGCTCGTTT
1381  TCGCTGGGGATGGAATTATTGTACCATTTTCTATCATGGAATATTTATAGGCCAGGGCAT
1441  GTGTATGTGTCTGCTAATGTAAACTTTGTCATGGTTTCCATTTACTAACAGCAACAGCAA
1501  GAAATAAATCAGAGAGCAAGGCATCGGGGGTGAATCTTGTCTAACATTCCCGAGGTCAGC
1561  CAGGCTGCTAACCTGGAAAGCAGGATGTAGTTCTGCCAGGCAACTTTTAAAGCTCATGCA
1621  TTTCAAGCAGCTGAAGAAAAAATCAGAACTAACCAGTACCTCTGTATAGAAATCTAAAAG
1681  AATTTTACCATTCAGTTAATTCAATGTGAACACTGGCACACTGCTCTTAAGAAACTATGA
1741  AGATCTGAGATTTTTTGTGTATGTTTTGACTCTTTTGAGTGGTAATCATATGTGTCTT
1801  TATAGATGTACATACCTCCTTGCACAAATGGAGGGGAATTCATTTTCATCACTGGGAGTG
1861  TCCTTAGTGTATAAAACCATGCTGGTATATGGCTTCAAGTTGTAAAAATGAAAGTGACT
1921  TTAAAAGAAAATAGGGGATGGTCCAGGATCTCCACTGATAAGACTGTTTTTAAGTAACTT
1981  AAGGACCTTTGGGTCTACAAGTATATGTGAAAAAAATGAGACTTACTGGGTGAGGAAATC
2041  CATTGTTTAAAGATGGTCGTGTGTGTGTGTGTGTGTGTGTGTGTGTGTTGTGTTGTGTTT
2101  TGTTTTTTAAGGGAGGGAATTTATTATTTACCGTTGCTTGAAATTACTGTGTAAATATAT
2161  GTCTGATAATGATTTGCTCTTTGACAACTAAAATTAGGACTGTATAAGTACTAGATGCAT
2221  CACTGGGTGTTGATCTTACAAGATATTGATGATAACACTTAAAATTGTAACCTGCATTTT
2281  TCACTTTGCTCTCAATTAAAGTCTATTCAAAA
```

| Zn++ Finger | | | | | | | | | | | | | |
|---|---|---|---|---|---|---|---|---|---|---|---|---|---|
| Consensus | TG E KPY / R F | X | C | XXXX | C | XXX | F | XXXXX | L | XX | H | XXX | H |
| WT33 #1 | RPF | M | C | AYPG | C | NKRY | F | KLSH- | L | QM | H | SRK | H |
| EGR1 #1 | PH E RPY | A | C | PVES | C | NRR | F | SRSDE | L | TR | H | IRI | H |
| WT33 #2 | TG E KPY | Q | C | DFKD | C | ERR | F | SRSDQ* | L | KR | H | QRR | H |
| EGR2 #1 | VH Q RPY | P | C | PAQG | C | NRR | F | SRSDQ | L | TR | H | IRI | H |
| EGR1 #2 | TG Q KPF | Q | C | --RI | C | MRN | F | SRSDH | L | TT | H | IRT | H |
| WT33 #3 | TG V KPF | Q | C | --LT | C | QRK | F | SRSNH | L | KT | H | TRT | H |
| EGR2 #2 | TG H KPF | Q | C | --RI | C | MRN | F | SRSDQ | L | TT | H | IRT | H |
| EGR1 #3 | TG E KPF | A | C | --DI | C | GRK | F | ARSDE | R | KR | H | TKI | H |
| WT33 #4 | TG Q-Q KPF | S | C | RWPS | C | QKK | F | ARSDE | L | VR | H | HNM | H |
| EGR2 #3 | TG KPF | A | C | --DY | C | GRK | F | ARSDE | R | KR | H | TKI | H |

```
TGTGTGAATGGAGCGGCCGAGCATCCTGGCTCCTCCTCCTTCCCTGCTGCCGGCCCCTCT     60
TATTTGAGCTTTGGGAAGCTGGGGGCAGCCAGGCAGCTGGGGTAAGGAGTTCAAGGCAGC    120
GCCCACACCCGGGGCTCTCCGCAACCCGACCGCCTGCCTGCCTCCCCCTTTCCTTTTTTC    180
CCCGCCCCTCCCTCCCACCCACTCATTCACCCACCCACCCAGAGAGAGGACGGCAGCCCA    240
GGAACCCGGGCCCGCCGCCTCCTCGCCGCCGATCCTGGACTTCCTCCTGTCGCAGGAGCCG    300
GCTTCCACGTGTGTCCCGGAGCCGGCGTCTCAGCACACGCTCCGCCGGGAGCCCGGGTGC    360
GTCCAGCAGCCGGAGCAACCTGGGGACCGAGGCCCCCGGAGCGCCTGGGCCAAGTCCAGC    420
                                                        M        1
GCCGAGAATCCGCAGGATCGCAGGAGCGGAGAACCGTCCGCATCCGAGCCGCACCTCATG    480

G  S  D  V  R  D  L  N  A  L  L  P  A  V  S  S  L  G  G  G    21
GGTTCCGACGTGCGGGACCTGAACGCGCTGCTGCCCGCTGTGTCTTCGCTGGGCGGCGGC    540

G  G  G  C  G  L  P  V  S  G  A  R  Q  W  A  P  V  L  D  F    41
GGCGGCGGCTGCGGGCTCCCTGTGAGCGGCGCACGGCAGTGGGCGCCCGTGTTGGACTTC    600

A  P  P  G  A  S  A  Y  G  S  L  G  G  P  A  P  P  P  A  P    61
GCGCCTCCGGGCGCCTCGGCTTACGGGTCGCTGGGCGGTCCCGCGCCTCCTCCCGCTCCG    660

P  P  P  P  P  P  H  S  F  I  K  Q  E  P  S  W  G  G  A      81
CCGCCGCCTCCGCCGCCACCCCACTCCTTCATCAAACAGGAGCCCAGCTGGGGCGGCGCC    720

E  P  H  E  E  O  C  L  S  A  F  T  L  H  F  S  G  Q  F  T   101
GAGCCACACGAGGAGCAGTGCCTGAGCGCCTTCACCTTGCACTTCTCGGGCCAGTTCACC    780

G  T  A  G  A  C  R  Y  G  P  F  G  P  P  P  P  S  Q  A  S   121
GGTACAGCCGGGGCCTGTCGCTACGGACCCTTCGGTCCTCCCCCGCCCAGCCAGGCGTCC    840

S  G  Q  A  R  M  F  P  N  A  P  Y  L  P  S  C  L  E  S  Q   141
TCGGGCCAGGCCAGGATGTTCCCCAATGCGCCCTACCTGCCCAGCTGCCTGGAGAGCCAG    900

P  T  I  R  N  Q  G  Y  S  T  V  T  F  D  G  A  P  S  Y  G   161
CCTACCATCCGCAACCAAGGATACAGCACGGTCACTTTCGACGGGGCGCCCAGCTATGGC    960

H  T  P  S  H  H  A  A  Q  F  P  N  H  S  F  K  H  E  D  P   181
CACACGCCCTCGCATCACGCGGCGCAGTTCCCCAACCATTCCTTCAAACACGAGGACCCC   1020

M  G  Q  Q  G  S  L  G  E  Q  Q  Y  S  V  P  P  P  V  Y  G   201
ATGGGCCAGCAGGGCTCGCTGGGCGAGCAGCAGTACTCCGTGCCACCTCCGGTGTATGGC   1080

C  H  T  P  T  D  S  C  T  G  S  Q  A  L  L  L  R  T  P  Y   221
TGCCACACCCCTACTGACAGTTGCACAGGCAGCCAGGCCCTGCTCCTGAGGACGCCCTAC   1140

S  S  D  N  L  Y  Q  M  T  S  Q  L  E  C  M  T  W  N  Q  M   241
AGCAGTGACAATTTATACCAAATGACCTCCCAGCTTGAATGCATGACCTGGAATCAGATG   1200

N  L  G  A  T  L  K  G  M  A  A  G  S  S  S  S  V  K  W  T   261
AACCTAGGAGCTACCTTAAAGGGAATGGCTGCTGGGAGCTCCAGCTCAGTGAAATGGACA   1260

E  G  Q  S  N  H  G  T  G  Y  E  S  E  N  H  T  A  P  I  L   281
GAAGGGCAGAGCAACCACGGCACAGGGTACGAGAGTGAGAACCACACGGCCCCCATCCTC   1320
```

Figure 9A

```
C   G   A   Q   Y   R   I   H   T   H   G   V   F   R   G   I   Q   D   V   R        301
TGTGGTGCCCAGTACAGAATACACACCCACGGGGTCTTCCGAGGCATTCAGGATGTGCGG                         1380

R   V   S   G   V   A   P   T   L   V   R   S   A   S   E   T   S   E   K   R        321
CGTGTATCTGGAGTGGCCCCAACTCTTGTCCGGTCAGCATCTGAAACCAGTGAGAAACGT                         1440

P   F   M   C   A   Y   P   G   C   N   K   R   Y   F   K   L   S   H   L   Q        341
CCTTTCATGTGTGCATACCCAGGCTGCAATAAGAGATATTTTAAGCTGTCCCACTTACAG                         1500

M   H   S   R   K   H   I   G   E   K   P   Y   Q   C   D   F   K   D   C   E        361
ATGCATAGCCGGAAGCACACTGGTGAGAAACCATACCAGTGTGACTTCAAGGACTGCGAG                         1560

R   R   F   S   R   S   D   Q   L   K   R   H   Q   R   R   H   T   G   V   K        381
AGAAGGTTTTCTCGCTCAGACCAGCTCAAAAGACACCAAAGGAGACACACAGGTGTGAAA                         1620

P   F   Q   C   K   T   C   Q   R   K   F   S   R   S   D   H   L   K   T   H        401
CCATTCCAGTGTAAAACTTGTCAGCGAAAGTTTTCCCGGTCCGACCATCTGAAGACCCAC                         1680

T   R   T   H   T   G   K   T   S   E   K   P   F   S   C   R   W   H   S   C        421
ACCAGGACTCATACAGGTAAAACAAGTGAAAAGCCCTTCAGCTGTCGGTGGCACAGTTGT                         1740

Q   K   K   F   A   R   S   D   E   L   V   R   H   H   N   M   H   Q   R   N        441
CAGAAAAAGTTTGCGCGCTCAGACGAATTGGTCCGCCATCACAACATGCATCAGAGAAAC                         1800

M   T   K   L   H   V   A   L                                                         419
ATGACCAAACTCCACGTGGCGCTTTGAGGGGTCCGACACGGAGACAGTCCAGCATCCCAG                         1860

GCAGGAAAGTGTGCAAACTGCTTCCAAATCTGATTTTGAAATTCCTCCCACTCACCTTTC                         1920
AAAGGACACGACTGTGGATCTACATCCGACTTCCAAGACAGCACACCTGATTGACTGCAT                         1980
CCTATCAGGTTTGCCGGAAGGAGTCGGTCCTCCGCCCACTTTTGATTAACTCACAGGCCT                         2040
GAAAAAAGTGGTTCAAGGTGTCTAGAAAGTCCAATTGTCTGAATTTTCTACTGTTAGAAG                         2100
AACCATTGTTGATAATGCCCCCCGCCCCCCCCCCCGGGTTTCCTCTTCTCCTTTGTG                            2160
ATCATTTCCCCAGGATTAGAGAGACTGTTACATTTTCTTTCATGGGATATTTATAGGCCA                         2220
GGGCATGTGTATGTGCCTGCTAATGTAAACTCTGTCATAGTTCCCATTTACTAACTGCCC                         2280
TAGAAAGAAATAAATCAGAGAGCAAGGCACCAGGCAAGAATCGTACAGAATTTCAGAGGT                         2340
CTGGCTGCAAACCTGGAAACCTGGAAGGCAGATGTAATTCTACAGGCGATTGTTAAAGC                          2400
TCATAGGTTTTGAGTAACTGCATAGTAGGTTGGTATTAACTAGAACTCTGTATAGTTAGG                         2460
ACGGAGAGGAGCCTTCCTGCTCAGCTATTCACTCTGAACACTAGCACTGGGCTCTTAAGA                         2520
AATGATGTTTAAGAGCAGAGATCTTTTTTTAATGTCTTTGATTTATTTTTAGTTGTAA                           2580
TTAGGTACATCCTCAGAGATGTACTTTCCTCCTCTTGTGCAGGATGTGGAGGACTCGTTC                         2640
CATCATCTGGGGCATCTTTAGAGTGTATAGACCACACTGGTTATGTGGCTTCAAGTTGTA                         2700
AAAATTAAAATGACTTTAAAAGAAACTAGGGGCTGGTCCAGGATCTCACTGGTAAGACTG                         2760
TTCTTAAGTAACTTAAGTATCTTTGAATCTGCAAGTATGTAGGGAAAAAAAAAAGATAT                          2820
ATTATTGTGAGGAAATCCATTGTTTAAAGGTGTGCGTGTGTTGTTGTTTTTTAAAGG                            2880
GAGGGAGTTTATTATTTACTGTAGCTTGAAATACTGTGTAAATATATATGTATATATATG                         2940
ATGTGCTCTTTGTCAACTAAAATTAGGAGGTGTATGGTATTAGCTGCATCACTGTGTGGA                         3000
TGTCAATCTTACAGTGTATTGATGATAATACTAAAAATGTAACCTGCATCTTTTTCCACT                         3060
TGGCTGTCAATTAAAGTCTATTCAAAAGGA                                                       3089
```

Figure 9B

```
MGSDVRDLNALLPAVPSL-GGGGGCALPVSGAAQWAPVLDFAPPGASAYGSLGGPAPPPA      59
||||||||||||||||||  ||||||| ||||||| ||||||||||||||||||||||||
MGSDVRDLNALLPAVSSLGGGGGGCGLPVSGARQWAPVLDFAPPGASAYGSLGGPAPPPA      60

PPPPPPPPPHSFIKQEPSWGGAEPHEEQCLSAFTVHFSGQFTGTAGACRYGPFGPPPPSQ     119
|||||||||||||||||||||||||||||||||||| |||||||||||||||||||||||
-PPPPPPPPHSFIKQEPSWGGAEPHEEQCLSAFTLHFSGQFTGTAGACRYGPFGPPPPSQ     119

ASSGQARMFPNAPYLPSCLESQPAIRNQGYSTVTFDGTPSYGHTPSHHAAQFPNHSFKHE     179
|||||||||||||||||||||||| ||||||||||||  |||||||||||||||||||||
ASSGQARMFPNAPYLPSCLESQPTIRNQGYSTVTFDGAPSYGHTPSHHAAQFPNHSFKHE     179

DPMGQQGSLGEQQYSVPPPVYGCHTPTDSCTGSQALLLRTPYSSDNLYQMTSQLECMTWN     239
||||||||||||||||||||||||||||||||||||||||||||||||||||||||||||
DPMGQQGSLGEQQYSVPPPVYGCHTPTDSCTGSQALLLRTPYSSDNLYQMTSQLECMTWN     239

QMNLGATLKGVAAGSSSSVKWTEGQSNHSTGYESDNHTTPILCGAQYRIHTHGVFRGIQ      298
|||||||||| |||||||||||||||||  ||||| | |||||||||||||||||||||
QMNLGATLKGMAAGSSSSVKWTEGQSNHGIGYESENHTAPILCGAQYRIHTHGVFRGIQ      298

DVRRVPGVAPTLVRSASETSEKRPFMCAYPGCNKRYFKLSHLQMHSRKHTGEKPYQCDFK     358
||||| |||||||||||||||||||||||||||||||||||||||||||||||||||||
DVRRVSGVAPTLVRSASETSEKRPFMCAYPGCNKRYFKLSHLQMHSRKHTGEKPYQCDFK     358

DCERRFSRSDQLKRHQRRHTGVKPFQCKTCQRKFSRSDHLKTHTRTHTGKTSEKPFSCR      417
||||||||||||||||||||||||||||||||||||||||||||||||||||||||||||
DCERRFSRSDQLKRHQRRHTGVKPFQCKTCQRKFSRSDHLKTHTRTHTGKTSEKPFSCR      417

WPSCQKKFARSDELVRHHNMHQRNMTKLQLAL      449
| ||||||||||||||||||||||||||  ||
WHSCQKKFARSDELVRHHNMHQRNMTKLHVAL      449
```

Figure 10

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 2312 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..1035

( x i ) SEQUENCE DESCRIPTION: SEQ ID NO:1:

```
GAG GAG CAG TGC CTG AGC GCC TTC ACT GTC CAC TTT TCC GGC CAG TTC     48
Glu Glu Gln Cys Leu Ser Ala Phe Thr Val His Phe Ser Gly Gln Phe
 1               5                  10                  15

ACT GGC ACA GCC GGA GCC TGT CGC TAC GGG CCC TTC GGT CCT CCT CCG     96
Thr Gly Thr Ala Gly Ala Cys Arg Tyr Gly Pro Phe Gly Pro Pro Pro
             20                  25                  30

CCC AGC CAG GCG TCA TCC GGC CAG GCC AGG ATG TTT CCT AAC GCG CCC    144
Pro Ser Gln Ala Ser Ser Gly Gln Ala Arg Met Phe Pro Asn Ala Pro
         35                  40                  45

TAC CTG CCC AGC TGC CTC GAG AGC CAG CCC GCT ATT CGC AAT CAG GGT    192
Tyr Leu Pro Ser Cys Leu Glu Ser Gln Pro Ala Ile Arg Asn Gln Gly
     50                  55                  60

TAC AGC ACG GTC ACC TTC GAC GGG ACG CCC AGC TAC GGT CAC ACG CCC    240
Tyr Ser Thr Val Thr Phe Asp Gly Thr Pro Ser Tyr Gly His Thr Pro
 65                  70                  75                  80

TCG CAC CAT GCG GCG CAG TTC CCC AAC CAC TCA TTC AAG CAT GAG GAT    288
Ser His His Ala Ala Gln Phe Pro Asn His Ser Phe Lys His Glu Asp
                 85                  90                  95

CCC ATG GGC CAG CAG GGC TCG CTG GGT GAG CAG CAG TAC TCG GTG CCG    336
Pro Met Gly Gln Gln Gly Ser Leu Gly Glu Gln Gln Tyr Ser Val Pro
            100                 105                 110

CCC CCG GTC TAT GGC TGC CAC ACC CCC ACC GAC AGC TGC ACC GGC AGC    384
Pro Pro Val Tyr Gly Cys His Thr Pro Thr Asp Ser Cys Thr Gly Ser
        115                 120                 125

CAG GCT TTG CTG CTG AGG ACG CCC TAC AGC AGT GAC AAT TTA TAC CAA    432
Gln Ala Leu Leu Leu Arg Thr Pro Tyr Ser Ser Asp Asn Leu Tyr Gln
    130                 135                 140

ATG ACA TCC CAG CTT GAA TGC ATG ACC TGG AAT CAG ATG AAC TTA GGA    480
Met Thr Ser Gln Leu Glu Cys Met Thr Trp Asn Gln Met Asn Leu Gly
145                 150                 155                 160

GCC ACC TTA AAG GGC CAC AGC ACA GGG TAC GAG AGC GAT AAC CAC ACA    528
Ala Thr Leu Lys Gly His Ser Thr Gly Tyr Glu Ser Asp Asn His Thr
                165                 170                 175
```

| | | | | | | | | | | | | | | | | |
|---|---|---|---|---|---|---|---|---|---|---|---|---|---|---|---|---|
| ACG | CCC | ATC | CTC | TGC | GGA | GCC | CAA | TAC | AGA | ATA | CAC | ACG | CAC | GGT | GTC | 576 |
| Thr | Pro | Ile | Leu | Cys | Gly | Ala | Gln | Tyr | Arg | Ile | His | Thr | His | Gly | Val | |
| | | | 180 | | | | | 185 | | | | | 190 | | | |
| TTC | AGA | GGC | ATT | CAG | GAT | GTG | CGA | CGT | GTG | CCT | GGA | GTA | GCC | CCG | ACT | 624 |
| Phe | Arg | Gly | Ile | Gln | Asp | Val | Arg | Arg | Val | Pro | Gly | Val | Ala | Pro | Thr | |
| | | 195 | | | | | 200 | | | | | 205 | | | | |
| CTT | GTA | CGG | TCG | GCA | TCT | GAG | ACC | AGT | GAG | AAA | CGC | CCC | TTC | ATG | TGT | 672 |
| Leu | Val | Arg | Ser | Ala | Ser | Glu | Thr | Ser | Glu | Lys | Arg | Pro | Phe | Met | Cys | |
| | 210 | | | | | 215 | | | | | 220 | | | | | |
| GCT | TAC | CCA | GGC | TGC | AAT | AAG | AGA | TAT | TTT | AAG | CTG | TCC | CAC | TTA | CAG | 720 |
| Ala | Tyr | Pro | Gly | Cys | Asn | Lys | Arg | Tyr | Phe | Lys | Leu | Ser | His | Leu | Gln | |
| 225 | | | | | 230 | | | | | 235 | | | | | 240 | |
| ATG | CAC | AGC | AGG | AAG | CAC | ACT | GGT | GAG | AAA | CCA | TAC | CAG | TGT | GAC | TTC | 768 |
| Met | His | Ser | Arg | Lys | His | Thr | Gly | Glu | Lys | Pro | Tyr | Gln | Cys | Asp | Phe | |
| | | | | 245 | | | | | 250 | | | | | 255 | | |
| AAG | GAC | TGT | GAA | CGA | AGG | TTT | TTT | CGT | TCA | GAC | CAG | CTC | AAA | AGA | CAC | 816 |
| Lys | Asp | Cys | Glu | Arg | Arg | Phe | Phe | Arg | Ser | Asp | Gln | Leu | Lys | Arg | His | |
| | | | 260 | | | | | 265 | | | | | 270 | | | |
| CAA | AGG | AGA | CAT | ACA | GGT | GTG | AAA | CCA | TTC | CAG | TGT | AAA | ACT | TGT | CAG | 864 |
| Gln | Arg | Arg | His | Thr | Gly | Val | Lys | Pro | Phe | Gln | Cys | Lys | Thr | Cys | Gln | |
| | | 275 | | | | | 280 | | | | | 285 | | | | |
| CGA | AAG | TTC | TCC | CGG | TCC | GAC | CAC | CTG | AAG | ACC | CAC | ACC | AGG | ACT | CAT | 912 |
| Arg | Lys | Phe | Ser | Arg | Ser | Asp | His | Leu | Lys | Thr | His | Thr | Arg | Thr | His | |
| | 290 | | | | | 295 | | | | | 300 | | | | | |
| ACA | GGT | GAA | AAG | CCC | TTC | AGC | TGT | CGG | TGG | CCA | AGT | TGT | CAG | AAA | AAG | 960 |
| Thr | Gly | Glu | Lys | Pro | Phe | Ser | Cys | Arg | Trp | Pro | Ser | Cys | Gln | Lys | Lys | |
| 305 | | | | | 310 | | | | | 315 | | | | | 320 | |
| TTT | GCC | CGG | TCA | GAT | GAA | TTA | GTC | CGC | CAT | CAC | AAC | ATG | CAT | CAG | AGA | 1008 |
| Phe | Ala | Arg | Ser | Asp | Glu | Leu | Val | Arg | His | His | Asn | Met | His | Gln | Arg | |
| | | | | 325 | | | | | 330 | | | | | 335 | | |
| AAC | ATG | ACC | AAA | CTC | CAG | CTG | GCG | CTT | TGAGGGGTCT | | CCCTCGGGGA | | | | | 1055 |
| Asn | Met | Thr | Lys | Leu | Gln | Leu | Ala | Leu | | | | | | | | |
| | | | 340 | | | | | 345 | | | | | | | | |

| | | | | |
|---|---|---|---|---|
| CCGTTCAGTG | TCCCAGGCAG | CACAGTGTGT | GAACTGCTTT | CAAGTCTGAC | TCTCCACTCC | 1115 |
| TCCTCACTAA | AAAGGAAACT | TCAGTTGATC | TTCTTCATCC | AACTTCCAAG | ACAAGATACC | 1175 |
| GGTGCTTCTG | GAAACTACCA | GGTGTGCCTG | GAAGAGTTGG | TCTCTGCCCT | GCCTACTTTT | 1235 |
| AGTTGACTCA | CAGGCCCTGG | AGAAGCAGCT | AACAATGTCT | GGTTAGTTAA | AAGCCCATTG | 1295 |
| CCATTTGGTG | TGGATTTTCT | ACTGTAAGAA | GAGCCATAGC | TGATCATGTC | CCCCTGACCC | 1355 |
| TTCCCTTCTT | TTTTTATGCT | CGTTTCGCT | GGGGATGGAA | TTATTGTACC | ATTTTCTATC | 1415 |
| ATGGAATATT | TATAGGCCAG | GGCATGTGTA | TGTGTCTGCT | AATGTAAACT | TTGTCATGGT | 1475 |
| TTCCATTTAC | TAACAGCAAC | AGCAAGAAAT | AAATCAGAGA | GCAAGGCATC | GGGGGTGAAT | 1535 |
| CTTGTCTAAC | ATTCCCGAGG | TCAGCCAGGC | TGCTAACCTG | GAAAGCAGGA | TGTAGTTCTG | 1595 |
| CCAGGCAACT | TTTAAAGCTC | ATGCATTTCA | AGCAGCTGAA | GAAAAAATCA | GAACTAACCA | 1655 |
| GTACCTCTGT | ATAGAAATCT | AAAAGAATTT | TACCATTCAG | TTAATTCAAT | GTGAACACTG | 1715 |
| GCACACTGCT | CTTAAGAAAC | TATGAAGATC | TGAGATTTTT | TTGTGTATGT | TTTGACTCT | 1775 |
| TTTGAGTGGT | AATCATATGT | GTCTTTATAG | ATGTACATAC | CTCCTTGCAC | AAATGGAGGG | 1835 |
| GAATTCATTT | TCATCACTGG | GAGTGTCCTT | AGTGTATAAA | AACCATGCTG | GTATATGGCT | 1895 |
| TCAAGTTGTA | AAAATGAAAG | TGACTTTAAA | AGAAAATAGG | GGATGGTCCA | GGATCTCCAC | 1955 |
| TGATAAGACT | GTTTTTAAGT | AACTTAAGGA | CCTTTGGGTC | TACAAGTATA | TGTGAAAAAA | 2015 |
| ATGAGACTTA | CTGGGTGAGG | AAATCCATTG | TTTAAAGATG | GTCGTGTGTG | TGTGTGTGTG | 2075 |
| TGTGTGTGTG | TGTTGTGTTG | TGTTTTGTTT | TTTAAGGGAG | GGAATTTATT | ATTTACCGTT | 2135 |

| GCTTGAAATT | ACTGTGTAAA | TATATGTCTG | ATAATGATTT | GCTCTTTGAC | AACTAAAATT | 2195 |
| AGGACTGTAT | AAGTACTAGA | TGCATCACTG | GGTGTTGATC | TTACAAGATA | TTGATGATAA | 2255 |
| CACTTAAAAT | TGTAACCTGC | ATTTTCACT | TTGCTCTCAA | TTAAAGTCTA | TTCAAAA | 2312 |

( 2 ) INFORMATION FOR SEQ ID NO:2:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Glu | Glu | Gln | Cys | Leu | Ser | Ala | Phe | Thr | Val | His | Phe | Ser | Gly | Gln | Phe |
| 1 | | | | 5 | | | | | 10 | | | | | 15 | |
| Thr | Gly | Thr | Ala | Gly | Ala | Cys | Arg | Tyr | Gly | Pro | Phe | Gly | Pro | Pro | Pro |
| | | | 20 | | | | 25 | | | | | 30 | | | |
| Pro | Ser | Gln | Ala | Ser | Ser | Gly | Gln | Ala | Arg | Met | Phe | Pro | Asn | Ala | Pro |
| | | | 35 | | | | 40 | | | | 45 | | | | |
| Tyr | Leu | Pro | Ser | Cys | Leu | Glu | Ser | Gln | Pro | Ala | Ile | Arg | Asn | Gln | Gly |
| | 50 | | | | | 55 | | | | | 60 | | | | |
| Tyr | Ser | Thr | Val | Thr | Phe | Asp | Gly | Thr | Pro | Ser | Tyr | Gly | His | Thr | Pro |
| 65 | | | | | 70 | | | | | 75 | | | | | 80 |
| Ser | His | His | Ala | Ala | Gln | Phe | Pro | Asn | His | Ser | Phe | Lys | His | Glu | Asp |
| | | | | 85 | | | | | 90 | | | | | 95 | |
| Pro | Met | Gly | Gln | Gln | Gly | Ser | Leu | Gly | Glu | Gln | Gln | Tyr | Ser | Val | Pro |
| | | | | 100 | | | | | 105 | | | | | 110 | |
| Pro | Pro | Val | Tyr | Gly | Cys | His | Thr | Pro | Thr | Asp | Ser | Cys | Thr | Gly | Ser |
| | | | 115 | | | | 120 | | | | | 125 | | | |
| Gln | Ala | Leu | Leu | Leu | Arg | Thr | Pro | Tyr | Ser | Ser | Asp | Asn | Leu | Tyr | Gln |
| | 130 | | | | | 135 | | | | | 140 | | | | |
| Met | Thr | Ser | Gln | Leu | Glu | Cys | Met | Thr | Trp | Asn | Gln | Met | Asn | Leu | Gly |
| 145 | | | | | 150 | | | | | 155 | | | | | 160 |
| Ala | Thr | Leu | Lys | Gly | His | Ser | Thr | Gly | Tyr | Glu | Ser | Asp | Asn | His | Thr |
| | | | | 165 | | | | | 170 | | | | | 175 | |
| Thr | Pro | Ile | Leu | Cys | Gly | Ala | Gln | Tyr | Arg | Ile | His | Thr | His | Gly | Val |
| | | | 180 | | | | | 185 | | | | | 190 | | |
| Phe | Arg | Gly | Ile | Gln | Asp | Val | Arg | Arg | Val | Pro | Gly | Val | Ala | Pro | Thr |
| | | 195 | | | | | 200 | | | | | 205 | | | |
| Leu | Val | Arg | Ser | Ala | Ser | Glu | Thr | Ser | Glu | Lys | Arg | Pro | Phe | Met | Cys |
| | 210 | | | | | 215 | | | | | 220 | | | | |
| Ala | Tyr | Pro | Gly | Cys | Asn | Lys | Arg | Tyr | Phe | Lys | Leu | Ser | His | Leu | Gln |
| 225 | | | | | 230 | | | | | 235 | | | | | 240 |
| Met | His | Ser | Arg | Lys | His | Thr | Gly | Glu | Lys | Pro | Tyr | Gln | Cys | Asp | Phe |
| | | | | 245 | | | | | 250 | | | | | 255 | |
| Lys | Asp | Cys | Glu | Arg | Arg | Phe | Phe | Arg | Ser | Asp | Gln | Leu | Lys | Arg | His |
| | | | 260 | | | | | 265 | | | | | 270 | | |
| Gln | Arg | Arg | His | Thr | Gly | Val | Lys | Pro | Phe | Gln | Cys | Lys | Thr | Cys | Gln |
| | | 275 | | | | | 280 | | | | | 285 | | | |
| Arg | Lys | Phe | Ser | Arg | Ser | Asp | His | Leu | Lys | Thr | His | Thr | Arg | Thr | His |
| | 290 | | | | | 295 | | | | | 300 | | | | |
| Thr | Gly | Glu | Lys | Pro | Phe | Ser | Cys | Arg | Trp | Pro | Ser | Cys | Gln | Lys | Lys |
| 305 | | | | | 310 | | | | | 315 | | | | | 320 |
| Phe | Ala | Arg | Ser | Asp | Glu | Leu | Val | Arg | His | His | Asn | Met | His | Gln | Arg |
| | | | | 325 | | | | | 330 | | | | | 335 | |

Asn Met Thr Lys Leu Gln Leu Ala Leu
         340                 345

( 2 ) INFORMATION FOR SEQ ID NO:3:

( i ) SEQUENCE CHARACTERISTICS:
        ( A ) LENGTH: 3090 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 478..1824

( x i ) SEQUENCE DESCRIPTION: SEQ ID NO:3:

```
TGTGTGAATG GAGCGGCCGA GCATCCTGGC TCCTCCTCCT TCCCTGCTGC CGGCCCCTCT      60

TATTTGAGCT TGGGAAGCT GGGGGCAGCC AGGCAGCTGG GGTAAGGAGT TCAAGGCAGC       120

GCCCACACCC GGGGCTCTCC GCAACCCGAC CGCCTGCCTG CCTCCCCCTT TCCTTTTTTC      180

CCCGCCCCTC CCTCCCACCC ACTCATTCAC CCACCCACCC AGAGAGAGGA CGGCAGCCCA      240

GGAACCCGGG CCCGCCGCCT CCTCGCCGCG ATCCTGGACT TCCTCCTGTC GCAGGAGCCG      300

GCTTCCACGT GTGTCCCGGA GCCGGCGTCT CAGCACACGC TCCGCCGGGA GCCCGGGTGC      360

GTCCAGCAGC CGGAGCAACC TGGGGACCGA GGCCCCCGGA GCGCCTGGGC CAAGTCCAGC      420

GCCGAGAATC CGCAGGATCG CAGGAGCGGA GAACCGTCCG CATCCGAGCC GCACCTC         477
```

```
ATG  GGT  TCC  GAC  GTG  CGG  GAC  CTG  AAC  GCG  CTG  CTG  CCC  GCT  GTG  TCT    525
Met  Gly  Ser  Asp  Val  Arg  Asp  Leu  Asn  Ala  Leu  Leu  Pro  Ala  Val  Ser
               350                      355                      360

TCG  CTG  GGC  GGC  GGC  GGC  GGC  GGC  TGC  GGG  CTC  CCT  GTG  AGC  GGC  GCA    573
Ser  Leu  Gly  Gly  Gly  Gly  Gly  Gly  Cys  Gly  Leu  Pro  Val  Ser  Gly  Ala
               365                      370                      375

CGG  CAG  TGG  GCG  CCC  GTG  TTG  GAC  TTC  GCG  CCT  CCG  GGC  GCC  TCG  GCT    621
Arg  Gln  Trp  Ala  Pro  Val  Leu  Asp  Phe  Ala  Pro  Pro  Gly  Ala  Ser  Ala
               380                      385                      390

TAC  GGG  TCG  CTG  GGC  GGT  CCC  GCG  CCT  CCT  CCC  GCT  CCG  CCG  CCG  CCT    669
Tyr  Gly  Ser  Leu  Gly  Gly  Pro  Ala  Pro  Pro  Pro  Ala  Pro  Pro  Pro  Pro
               395                      400                      405

CCG  CCG  CCA  CCC  CAC  TCC  TTC  ATC  AAA  CAG  GAG  CCC  AGC  TGG  GGC  GGC    717
Pro  Pro  Pro  Pro  His  Ser  Phe  Ile  Lys  Gln  Glu  Pro  Ser  Trp  Gly  Gly
410                      415                      420                      425

GCC  GAG  CCA  CAC  GAG  GAG  CAG  TGC  CTG  AGC  GCC  TTC  ACC  TTG  CAC  TTC    765
Ala  Glu  Pro  His  Glu  Glu  Gln  Cys  Leu  Ser  Ala  Phe  Thr  Leu  His  Phe
                    430                      435                      440

TCG  GGC  CAG  TTC  ACC  GGT  ACA  GCC  GGG  GCC  TGT  CGC  TAC  GGA  CCC  TTC    813
Ser  Gly  Gln  Phe  Thr  Gly  Thr  Ala  Gly  Ala  Cys  Arg  Tyr  Gly  Pro  Phe
                    445                      450                      455

GGT  CCT  CCC  CCG  CCC  AGC  CAG  GCG  TCC  TCG  GGC  CAG  GCC  AGG  ATG  TTC    861
Gly  Pro  Pro  Pro  Pro  Ser  Gln  Ala  Ser  Ser  Gly  Gln  Ala  Arg  Met  Phe
                    460                      465                      470

CCC  AAT  GCG  CCC  TAC  CTG  CCC  AGC  TGC  CTG  GAG  AGC  CAG  CCT  ACC  ATC    909
Pro  Asn  Ala  Pro  Tyr  Leu  Pro  Ser  Cys  Leu  Glu  Ser  Gln  Pro  Thr  Ile
     475                      480                      485

CGC  AAC  CAA  GGA  TAC  AGC  ACG  GTC  ACT  TTC  GAC  GGG  GCG  CCC  AGC  TAT    957
Arg  Asn  Gln  Gly  Tyr  Ser  Thr  Val  Thr  Phe  Asp  Gly  Ala  Pro  Ser  Tyr
490                      495                      500                      505

GGC  CAC  ACG  CCC  TCG  CAT  CAC  GCG  GCG  CAG  TTC  CCC  AAC  CAT  TCC  TTC   1005
Gly  His  Thr  Pro  Ser  His  His  Ala  Ala  Gln  Phe  Pro  Asn  His  Ser  Phe
                    510                      515                      520
```

```
AAA CAC GAG GAC CCC ATG GGC CAG CAG GGC TCG CTG GGC GAG CAG CAG       1053
Lys His Glu Asp Pro Met Gly Gln Gln Gly Ser Leu Gly Glu Gln Gln
            525             530                 535

TAC TCC GTG CCA CCT CCG GTG TAT GGC TGC CAC ACC CCT ACT GAC AGT       1101
Tyr Ser Val Pro Pro Pro Val Tyr Gly Cys His Thr Pro Thr Asp Ser
        540             545                 550

TGC ACA GGC AGC CAG GCC CTG CTC CTG AGG ACG CCC TAC AGC AGT GAC       1149
Cys Thr Gly Ser Gln Ala Leu Leu Leu Arg Thr Pro Tyr Ser Ser Asp
        555                 560             565

AAT TTA TAC CAA ATG ACC TCC CAG CTT GAA TGC ATG ACC TGG AAT CAG       1197
Asn Leu Tyr Gln Met Thr Ser Gln Leu Glu Cys Met Thr Trp Asn Gln
570             575                 580                 585

ATG AAC CTA GGA GCT ACC TTA AAG GGA ATG GCT GCT GGG AGC TCC AGC       1245
Met Asn Leu Gly Ala Thr Leu Lys Gly Met Ala Ala Gly Ser Ser Ser
            590                 595                 600

TCA GTG AAA TGG ACA GAA GGG CAG AGC AAC CAC GGC ACA GGG TAC GAG       1293
Ser Val Lys Trp Thr Glu Gly Gln Ser Asn His Gly Thr Gly Tyr Glu
            605                 610             615

AGT GAG AAC CAC ACG GCC CCC ATC CTC TGT GGT GCC CAG TAC AGA ATA       1341
Ser Glu Asn His Thr Ala Pro Ile Leu Cys Gly Ala Gln Tyr Arg Ile
        620             625             630

CAC ACC CAC GGG GTC TTC CGA GGC ATT CAG GAT GTG CGG CGT GTA TCT       1389
His Thr His Gly Val Phe Arg Gly Ile Gln Asp Val Arg Arg Val Ser
        635             640             645

GGA GTG GCC CCA ACT CTT GTC CGG TCA GCA TCT GAA ACC AGT GAG AAA       1437
Gly Val Ala Pro Thr Leu Val Arg Ser Ala Ser Glu Thr Ser Glu Lys
650             655                 660                 665

CGT CCT TTC ATG TGT GCA TAC CCA GGC TGC AAT AAG AGA TAT TTT AAG       1485
Arg Pro Phe Met Cys Ala Tyr Pro Gly Cys Asn Lys Arg Tyr Phe Lys
                670                 675             680

CTG TCC CAC TTA CAG ATG CAT AGC CGG AAG CAC ACT GGT GAG AAA CCA       1533
Leu Ser His Leu Gln Met His Ser Arg Lys His Thr Gly Glu Lys Pro
            685                 690             695

TAC CAG TGT GAC TTC AAG GAC TGC GAG AGA AGG TTT TCT CGC TCA GAC       1581
Tyr Gln Cys Asp Phe Lys Asp Cys Glu Arg Arg Phe Ser Arg Ser Asp
        700                 705                 710

CAG CTC AAA AGA CAC CAA AGG AGA CAC ACA GGT GTG AAA CCA TTC CAG       1629
Gln Leu Lys Arg His Gln Arg Arg His Thr Gly Val Lys Pro Phe Gln
        715                 720                 725

TGT AAA ACT TGT CAG CGA AAG TTT TCC CGG TCC GAC CAT CTG AAG ACC       1677
Cys Lys Thr Cys Gln Arg Lys Phe Ser Arg Ser Asp His Leu Lys Thr
730             735                 740                 745

CAC ACC AGG ACT CAT ACA GGT AAA ACA AGT GAA AAG CCC TTC AGC TGT       1725
His Thr Arg Thr His Thr Gly Lys Thr Ser Glu Lys Pro Phe Ser Cys
                750             755                 760

CGG TGG CAC AGT TGT CAG AAA AAG TTT GCG CGC TCA GAC GAA TTG GTC       1773
Arg Trp His Ser Cys Gln Lys Lys Phe Ala Arg Ser Asp Glu Leu Val
            765                 770             775

CGC CAT CAC AAC ATG CAT CAG AGA AAC ATG ACC AAA CTC CAC GTG GCG       1821
Arg His His Asn Met His Gln Arg Asn Met Thr Lys Leu His Val Ala
            780                 785             790

CTT TGAGGGGTCC GACACGGAGA CAGTCCAGCA TCCCAGGCAG GAAAGTGTGC            1874
Leu

AAACTGCTTC CAAATCTGAT TTTGAAATTC CTCCCACTCA CCTTTCAAAG GACACGACTG     1934

TGGATCTACA TCCGACTTCC AAGACAGCAC ACCTGATTGA CTGCATCCTA TCAGGTTTGC    1994

CGGAAGGAGT CGGTCCTCCG CCCACTTTTG ATTAACTCAC AGGCCTGAAA AAAGTGGTTC    2054

AAGGTGTCTA GAAAGTCCAA TTGTCTGAAT TTCTACTGT TAGAAGAACC ATTGTTGATA     2114
```

-continued

```
ATGCCCCCCG CCCCCCCCCC CCCCGGGTTT CCTCTTCTCC TTTGTGATCA TTTCCCCAGG    2174
ATTAGAGAGA CTGTTACATT TTCTTTCATG GGATATTTAT AGGCCAGGGC ATGTGTATGT    2234
GCCTGCTAAT GTAAACTCTG TCATAGTTCC CATTTACTAA CTGCCCTAGA AAGAAATAAA    2294
TCAGAGAGCA AGGCACCAGG CAAGAATCGT ACAGAATTTC AGAGGTCTGG CTGCAAACCT    2354
GGAAACCTGG AAGGCCAGAT GTAATTCTAC AGGCGATTGT TAAAGCTCAT AGGTTTTGAG    2414
TAACTGCATA GTAGGTTGGT ATTAACTAGA ACTCTGTATA GTTAGGACGG AGAGGAGCCT    2474
TCCTGCTCAG CTATTCACTC TGAACACTAG CACTGGGCTC TTAAGAAATG ATGTTTTAAG    2534
AGCAGAGATC TTTTTTTAAT GTCTTTGATT TATTTTTTAG TTGTAATTAG GTACATCCTC    2594
AGAGATGTAC TTTCCTCCTC TTGTGCAGGA TGTGGAGGAC TCGTTCCATC ATCTGGGGCA    2654
TCTTTAGAGT GTATAGACCA CACTGGTTAT GTGGCTTCAA GTTGTAAAAA TTAAAATGAC    2714
TTTAAAAGAA ACTAGGGGCT GGTCCAGGAT CTCACTGGTA AGACTGTTCT TAAGTAACTT    2774
AAGTATCTTT GAATCTGCAA GTATGTAGGG AAAAAAAAA AGATATATTA TTGTGAGGAA    2834
ATCCATTGTT TAAAGGTGTG CGTGTGTTGT TGTTGTTTTT TAAAGGGAGG GAGTTTATTA    2894
TTTACTGTAG CTTGAAATAC TGTGTAAATA TATATGTATA TATATGATGT GCTCTTTGTC    2954
AACTAAAATT AGGAGGTGTA TGGTATTAGC TGCATCACTG TGTGGATGTC AATCTTACAG    3014
TGTATTGATG ATAATACTAA AAATGTAACC TGCATCTTTT TCCACTTGGC TGTCAATTAA    3074
AGTCTATTCA AAAGGA                                                    3090
```

( 2 ) INFORMATION FOR SEQ ID NO:4:

( i ) SEQUENCE CHARACTERISTICS:
  ( A ) LENGTH: 449 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

```
Met Gly Ser Asp Val Arg Asp Leu Asn Ala Leu Leu Pro Ala Val Ser
 1               5                  10                  15

Ser Leu Gly Gly Gly Gly Gly Gly Cys Gly Leu Pro Val Ser Gly Ala
                20                  25                  30

Arg Gln Trp Ala Pro Val Leu Asp Phe Ala Pro Pro Gly Ala Ser Ala
            35                  40                  45

Tyr Gly Ser Leu Gly Gly Pro Ala Pro Pro Ala Pro Pro Pro
    50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Leu His Phe
                85                  90                  95

Ser Gly Gln Phe Thr Gly Thr Ala Gly Ala Cys Arg Tyr Gly Pro Phe
               100                 105                 110

Gly Pro Pro Pro Pro Ser Gln Ala Ser Ser Gly Gln Ala Arg Met Phe
           115                 120                 125

Pro Asn Ala Pro Tyr Leu Pro Ser Cys Leu Glu Ser Gln Pro Thr Ile
130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
               165                 170                 175

Lys His Glu Asp Pro Met Gly Gln Gln Gly Ser Leu Gly Glu Gln Gln
```

|     |     |     |     |     |     |     |     |     |     |     |     |     |     |
|---|---|---|---|---|---|---|---|---|---|---|---|---|---|
|     |     |     |     | 180 |     |     |     |     | 185 |     |     |     | 190 |

Tyr Ser Val Pro Pro Pro Val Tyr Gly Cys His Thr Pro Thr Asp Ser
         195             200                 205

Cys Thr Gly Ser Gln Ala Leu Leu Arg Thr Pro Tyr Ser Ser Asp
    210             215             220

Asn Leu Tyr Gln Met Thr Ser Gln Leu Glu Cys Met Thr Trp Asn Gln
225             230                 235                     240

Met Asn Leu Gly Ala Thr Leu Lys Gly Met Ala Ala Gly Ser Ser Ser
            245             250                     255

Ser Val Lys Trp Thr Glu Gly Gln Ser Asn His Gly Thr Gly Tyr Glu
            260             265                     270

Ser Glu Asn His Thr Ala Pro Ile Leu Cys Gly Ala Gln Tyr Arg Ile
            275             280                 285

His Thr His Gly Val Phe Arg Gly Ile Gln Asp Val Arg Arg Val Ser
    290             295                 300

Gly Val Ala Pro Thr Leu Val Arg Ser Ala Ser Glu Thr Ser Glu Lys
305             310                 315                     320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385             390                 395                     400

His Thr Arg Thr His Thr Gly Lys Thr Ser Glu Lys Pro Phe Ser Cys
                405             410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
        435                 440                 445

Leu ( 2 ) INFORMATION FOR SEQ ID NO:5:

( i ) SEQUENCE CHARACTERISTICS:
      ( A ) LENGTH: 154 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:5:

Gln Cys Leu Ser Ala Phe Thr Val His Phe Ser Gly Gln Phe Thr Gly
1               5                   10                  15

Thr Ala Gly Ala Cys Arg Tyr Gly Pro Phe Gly Pro Pro Pro Pro Ser
            20              25                  30

Gln Ala Ser Ser Gly Gln Ala Arg Met Phe Pro Asn Ala Pro Tyr Leu
        35              40                  45

Pro Ser Cys Leu Glu Ser Gln Pro Ala Ile Arg Asn Gln Gly Tyr Ser
    50                  55                  60

Thr Val Thr Phe Asp Gly Thr Pro Ser Tyr Gly His Thr Pro Ser His
65              70                  75                      80

5,726,288

-continued

| His | Ala | Ala | Gln | Phe | Pro | Asn | His | Ser | Phe | Lys | His | Glu | Asp | Pro | Met |
|  |  |  |  | 85 |  |  |  |  | 90 |  |  |  |  |  | 95 |

| Gly | Gln | Gln | Gly | Ser | Leu | Gly | Glu | Gln | Gln | Tyr | Ser | Val | Pro | Pro | Pro |
|  |  |  | 100 |  |  |  |  | 105 |  |  |  |  | 110 |  |  |

| Val | Tyr | Gly | Cys | His | Thr | Pro | Thr | Asp | Ser | Cys | Thr | Gly | Ser | Gln | Ala |
|  |  | 115 |  |  |  |  | 120 |  |  |  |  | 125 |  |  |  |

| Leu | Leu | Leu | Arg | Thr | Pro | Tyr | Ser | Ser | Asp | Asn | Tyr | Leu | Gln | Met | Thr |
|  | 130 |  |  |  |  | 135 |  |  |  |  | 140 |  |  |  |  |

| Ser | Gln | Leu | Glu | Cys | Met | Thr | Trp | Asn | Gln |
| 145 |  |  |  |  | 150 |  |  |  |  |

( 2 ) INFORMATION FOR SEQ ID NO:6:

( i ) SEQUENCE CHARACTERISTICS:
  ( A ) LENGTH: 449 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:6:

| Met | Gly | Ser | Asp | Val | Arg | Asp | Leu | Asn | Ala | Leu | Leu | Pro | Ala | Val | Pro |
| 1 |  |  |  | 5 |  |  |  |  | 10 |  |  |  |  | 15 |  |

| Ser | Leu | Gly | Gly | Gly | Gly | Gly | Cys | Ala | Leu | Pro | Val | Ser | Gly | Ala | Ala |
|  |  |  | 20 |  |  |  |  | 25 |  |  |  |  | 30 |  |  |

| Gln | Trp | Ala | Pro | Val | Leu | Asp | Phe | Ala | Pro | Pro | Gly | Ala | Ser | Ala | Tyr |
|  |  |  | 35 |  |  |  |  | 40 |  |  |  |  | 45 |  |  |

| Gly | Ser | Leu | Gly | Gly | Pro | Ala | Pro | Pro | Pro | Ala | Pro | Pro | Pro | Pro | Pro |
|  | 50 |  |  |  |  | 55 |  |  |  |  | 60 |  |  |  |  |

| Pro | Pro | Pro | Pro | His | Ser | Phe | Ile | Lys | Gln | Glu | Pro | Ser | Trp | Gly | Gly |
| 65 |  |  |  |  | 70 |  |  |  |  | 75 |  |  |  |  | 80 |

| Ala | Glu | Pro | His | Glu | Glu | Gln | Cys | Leu | Ser | Ala | Phe | Thr | Val | His | Phe |
|  |  |  |  | 85 |  |  |  |  | 90 |  |  |  |  | 95 |  |

| Ser | Gly | Gln | Phe | Thr | Gly | Thr | Ala | Gly | Ala | Cys | Arg | Tyr | Gly | Pro | Phe |
|  |  |  | 100 |  |  |  |  | 105 |  |  |  |  | 110 |  |  |

| Gly | Pro | Pro | Pro | Pro | Ser | Gln | Ala | Ser | Ser | Gly | Gln | Ala | Arg | Met | Phe |
|  |  | 115 |  |  |  |  | 120 |  |  |  |  | 125 |  |  |  |

| Pro | Asn | Ala | Pro | Tyr | Leu | Pro | Ser | Cys | Leu | Glu | Ser | Gln | Pro | Ala | Ile |
|  | 130 |  |  |  |  | 135 |  |  |  |  | 140 |  |  |  |  |

| Arg | Asn | Gln | Gly | Tyr | Ser | Thr | Val | Thr | Phe | Asp | Gly | Thr | Pro | Ser | Tyr |
| 145 |  |  |  |  | 150 |  |  |  |  | 155 |  |  |  |  | 160 |

| Gly | His | Thr | Pro | Ser | His | His | Ala | Ala | Gln | Phe | Pro | Asn | His | Ser | Phe |
|  |  |  |  | 165 |  |  |  |  | 170 |  |  |  |  | 175 |  |

| Lys | His | Glu | Asp | Pro | Met | Gly | Gln | Gln | Gly | Ser | Leu | Gly | Glu | Gln | Gln |
|  |  |  | 180 |  |  |  |  | 185 |  |  |  |  | 190 |  |  |

| Tyr | Ser | Val | Pro | Pro | Pro | Val | Tyr | Gly | Cys | His | Thr | Pro | Thr | Asp | Ser |
|  |  | 195 |  |  |  |  | 200 |  |  |  |  | 205 |  |  |  |

| Cys | Thr | Gly | Ser | Gln | Ala | Leu | Leu | Leu | Arg | Thr | Pro | Tyr | Ser | Ser | Asp |
|  | 210 |  |  |  |  | 215 |  |  |  |  | 220 |  |  |  |  |

| Asn | Leu | Tyr | Gln | Met | Thr | Ser | Gln | Leu | Glu | Cys | Met | Thr | Trp | Asn | Gln |
| 225 |  |  |  |  | 230 |  |  |  |  | 235 |  |  |  |  | 240 |

| Met | Asn | Leu | Gly | Ala | Thr | Leu | Lys | Gly | Val | Ala | Ala | Gly | Ser | Ser | Ser |
|  |  |  |  | 245 |  |  |  |  | 250 |  |  |  |  | 255 |  |

| Ser | Val | Lys | Trp | Thr | Glu | Gly | Gln | Ser | Asn | His | Ser | Thr | Gly | Tyr | Glu |
|  |  |  | 260 |  |  |  |  | 265 |  |  |  |  | 270 |  |  |

| Ser | Asp | Asn | His | Thr | Thr | Pro | Ile | Leu | Cys | Gly | Ala | Gln | Tyr | Arg | Ile |

|  | 275 |  |  |  |  | 280 |  |  |  |  | 285 |  |  |  |
|---|---|---|---|---|---|---|---|---|---|---|---|---|---|---|
| His | Thr 290 | His | Gly | Val | Phe | Arg 295 | Gly | Ile | Gln | Asp | Val 300 | Arg | Arg | Val | Pro |
| Gly 305 | Val | Ala | Pro | Thr | Leu 310 | Val | Arg | Ser | Ala | Ser 315 | Glu | Thr | Ser | Glu | Lys 320 |
| Arg | Pro | Phe | Met | Cys 325 | Ala | Tyr | Pro | Gly | Cys 330 | Asn | Lys | Arg | Tyr | Phe 335 | Lys |
| Leu | Ser | His | Leu 340 | Gln | Met | His | Ser | Arg 345 | Lys | His | Thr | Gly | Glu 350 | Lys | Pro |
| Tyr | Gln | Cys 355 | Asp | Phe | Lys | Asp | Cys 360 | Glu | Arg | Arg | Phe | Ser 365 | Arg | Ser | Asp |
| Gln | Leu 370 | Lys | Arg | His | Gln | Arg 375 | Arg | His | Thr | Gly | Val 380 | Lys | Pro | Phe | Gln |
| Cys 385 | Lys | Thr | Cys | Gln | Arg 390 | Lys | Phe | Ser | Arg | Ser 395 | Asp | His | Leu | Lys | Thr 400 |
| His | Thr | Arg | Thr | His 405 | Thr | Gly | Lys | Thr | Ser 410 | Glu | Lys | Pro | Phe | Ser 415 | Cys |
| Arg | Trp | Pro | Ser 420 | Cys | Gln | Lys | Lys | Phe 425 | Ala | Arg | Ser | Asp | Glu 430 | Leu | Val |
| Arg | His | His 435 | Asn | Met | His | Gln | Arg 440 | Asn | Met | Thr | Lys | Leu 445 | Gln | Leu | Ala |
| Leu |  |  |  |  |  |  |  |  |  |  |  |  |  |  |  |

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:7:

| Val 1 | Ala | Ala | Gly | Ser 5 | Ser | Ser | Ser | Val | Lys 10 | Trp | Thr | Glu | Gly | Gln 15 | Ser |
|---|---|---|---|---|---|---|---|---|---|---|---|---|---|---|---|
| Asn |  |  |  |  |  |  |  |  |  |  |  |  |  |  |  |

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:8:

| Leu 1 | Gly | Ala | Thr | Leu 5 | Lys | Gly | His | Ser | Thr 10 | Gly | Tyr | Glu | Ser | Asp 15 |

LOCALIZATION AND CHARACTERIZATION OF THE WILMS' TUMOR GENE

The present application is a continuation-in-part of U.S. Ser. No. 07/614,161, filed Nov. 13, 1990, now abandoned, which is a continuation-in-part of U.S. Ser. No. 07/435,780 filed on Nov. 13, 1989, now abandoned, the contents of which are herein incorporated by reference.

FUNDING

Work described herein was funded by the National Institutes of Health, the Medical Research Council of Canada and the National Cancer Institute.

BACKGROUND

Wilms' tumor (WT) is an embryonal malignancy of the kidney which affects approximately 1 in 10,000 infants and young children. Matsunaga, *Human Genetics*, 57:231–246 (1981). The molecular basis of Wilms' tumor is not well understood.

The majority of WTs are sporadic tumors (>95%). A small set of WTs occur in a hereditary setting as familial cases or as part of cogential disorders such as the WAGR syndrome. Wilms' tumor (W) cases (approximately 2%) can occur in association with aniridia (A), a defect in the development of the iris, as well as genitourinary (G) abnormalities and mental retardation (R). Miller et al., *New Engl. J. Med.*, 270:922–927 (1964). These disorders form the WAGR syndrome, and can be attributed to a constitutional deletion of DNA in band 11p13 on human chromosome 11 in a group of genes known as the WAGR complex. Riccardi, et al., *Pediatrics*, 61:604–610 (1978); Francke, et al., *Cytogenet. Cell Genet.*, 24: 185–192 (1979). In these cases, bilateral Wilms' tumors are frequently observed, as are dysplastic changes in surrounding renal tissue (nephroblastomatosis) which are though to precede malignant transformation (i.e., precancerous conditions). Bove and McAdams, *Perspectives on Pediatric Pathol.*, 3:185–223 (1976). As a recessive oncogene or anti-oncogene, the Wilms' tumor locus is thought to curtail the growth of undifferentiated nephrotic cells. The genetics of WT generally conform to the two-hit mutational model of carcinogenesis used to describe the retinoblastoma locus on chromosome 13q. According to this concept, the rate-limiting events in tumor formation are two mutations. Sporadic tumors develop following two independent events, while familial cases involve transmission of one altered gene in the germline and a somatic mutation in the second gene. Hereditary cases display both a high penetrance and an increased incidence of bilateral cancers, attesting to the frequency of the somatic second event.

Observations have lead to the conclusion that at least in a subset of Wilms' tumors, the inactivation of a gene in 11p13, analogous to the retinoblastoma (RB) gene, is a key event in tumor formation. Considerable effort has been expended in attempting to localize the gene responsible for WT, as is evidence by the numerous reports describing such efforts. The localization of a Wilms' tumor gene at 11p13 is supported by the fact that 40–60% of individuals with the WAGR syndrome develop Wilms' tumor.

However, it appears that the genetics of Wilms' tumor are more complex than the two-hit mutational model. Based on additional research, it appears that Wilms' tumor may be caused by loss of function at alternative loci. In studies of two families showing hereditary predisposition to Wilms' tumor, linkage to 11p genetic markers was excluded, indicating the presence of at least one additional Wilms' tumor locus. Grundy, et al., *Nature*, 336:374–376 (1988); Huff, et al., *Nature*, 336:377–378 (1988). Further studies showed loss of heterozygosity in Wilms' tumors at 11p15 rather than 11p13. Reeve, et al., *Mol. Cell Biol.*, 9:1799–1803 (1989); Koufos, et al., *Am. J. Hum. Gen.*, 44:711–719 (1989); Koufos, et al., *Nature*, 309:170–172 (1984); Orkin, et al., *Nature*, 309:172–174 (1984); Reeve, et al., *Nature*, 309:174–176 (1984); Fearon, et al., *Nature*, 309:176–178 (1984). Although these data suggest the possibility of additional loci, the 11p13 Wilms' tumor locus is clearly associated with constitutional WAGR deletions and somatic chromosome rearrangements in a subset of sporadic tumors. Lewis, et al., *Genomics*, 3:25–31 (1988).

Despite considerable interest in identifying the Wilms' tumor gene and work focusing on doing so, to the present time, a transcript mapping to the region identified as containing the Wilms' tumor gene has not been identified.

SUMMARY OF THE INVENTION

The present invention relates to a method of analyzing cells for the Wilms' tumor gene, as well as to a method of analyzing cells for the Wilms' tumor gene transcript, the encoded polypeptides, and antibodies (polyclonal or monoclonal) which recognize all, or a portion of, the encoded polypeptides. As used herein, the term Wilms' tumor gene or Wilms' tumor locus refers to a specific gene in chromosome 11 band 13 (11p13) which is characteristicly altered in the WAGR syndrome or some sporadic Wilms' tumors (i.e., found in cells affected in these conditions), but which can reasonably be expected to be associated with or causative of other tumor types.

The present invention further relates to DNA sequences (SEQ ID NOS: 1 and 3), both genomic and cDNA clones, which map within the boundaries of constitutional and tumor deletions which physically define the Wilms' tumor locus on human chromosome 11 band p13 (11p13). For the first time, a gene which maps to the region containing the Wilms' tumor locus has been identified. The gene has been characterized and shown to span approximately 50 kb and to encode an mRNA (referred to as WT1 mRNA or transcript) approximately 3.1 kb in length. The WT1 mRNA has been shown to be expressed in a number of cell types. However, it is predominantly expressed in kidney and gonadal cells.

The amino acid sequence of the polypeptides encoded by the sequences have also been derived and features of the polypeptides have been examined (SEQ ID NOS: 2 and 4). Several of these features, such as the presence of four zinc finger domains and of a region rich in proline and glutamine (SEQ ID NO: 5), are indicative of a role in transcription regulation. The localization of the gene to 11p13, its tissue-specific expression and its predicted function, as well as the finding that this gene is specifically mutated in some Wilms' tumors, support the conclusion that it is the 11p13 Wilms' tumor gene. The present invention includes a method of identifying the Wilms' tumor gene; the isolated Wilms' tumor gene, the isolated gene transcript; the isolated encoded polypeptide; and diagnostic methods and reagents based thereon.

The present invention makes available for the first time a method of identifying in a sample, DNA which is clearly the 11p13 Wilms' tumor gene, an mRNA transcript thereof or a Wilms' tumor-encoded polypeptide, as well as materials (e.g., nucleic acid probes, anti-Wilms' tumor polypeptide antibodies) useful in these methods of identification. This is particularly valuable because the treatment of Wilms' tumor represents one of the clearest examples of success in pediatric oncology, as a result of the development of effective therapeutic regimens. However, for treatment to be most effective, the tumor must be diagnosed early. The present invention provides a means by which the risk of developing Wilms' tumor, for example, in diseases such as WAGR and Denys-Drash syndrome, can be assessed prior to its current method of detection. Often a Wilms' tumor mass is identified inadvertently by a parent when bathing the child. A diagnostic test would allow much earlier detection of the disease. The presence of the disease, once it has occurred, can be confirmed, thus making it possible to intervene therapeutically prior to or at an earlier stage in the development of the disease. It also provides a method by which the alteration of the WT1 gene can be detected in other tumor types which are known to express the WT1 transcript (e.g., leukemia cells, testicular tumors, ovarian tumors), using DNA probes or antibodies specific for Wilms' tumor gene-encoded polypeptide.

BRIEF DESCRIPTION OF THE FIGURES

FIG. 3 shows the nucleotide sequence of WT33 cDNA (SEQ ID NO: 1) and the predicted amino acid sequence (SEQ ID NO: 2) of the open reading frame extending from nucleotide 1 to 1035. The proline and glutamine residues in the proline/glutamine rich region (nucleotides 6 to 468) are boxed and the amino acids of the four zinc fingers (nucleotides 670 to 1002) which fit the zinc finger consensus are underlined.

FIG. 5 is a schematic map showing a comparison of the sequence derived from WT33 to the zinc finger consensus region and the sequence of human EGR1 and EGR2 genes.

FIG. 6 shows the results of Southern blot analyses of hybridization of Wilms' tumor cDNA with various DNA.

FIG. 6B shows the results of Southern blot analysis of Wit-13 hybrid cell lines digested with EcoRI and hybridized with WT2.

FIG. 9A and 9B shows the complete nucleic acid sequence of a composite sequence of mouse cDNAs derived from alternatively spliced mRNAs (SEQ ID NO: 3) and its predicted amino acid sequence (SEQ ID NO: 4). The sequences produced by alternative splicing are underlined and the region of the polypeptide spanning the gene zinc finger domains is boxed. This nucleic acid sequence is herein referred to as the WT1 sequence. (GenBank accession number M55512).

FIG. 10 shows the amino acid sequence comparison of the predicted WT1 polypeptides of humans (SEQ ID NO: 6) and mice (SEQ ID NO: 4). Amino acid identity between the two proteins is indicated by a vertical bar. The alternative splices are boxed, and their positions indicated by a vertical bar.

DETAILED DESCRIPTION OF THE INVENTION

Figure 1:
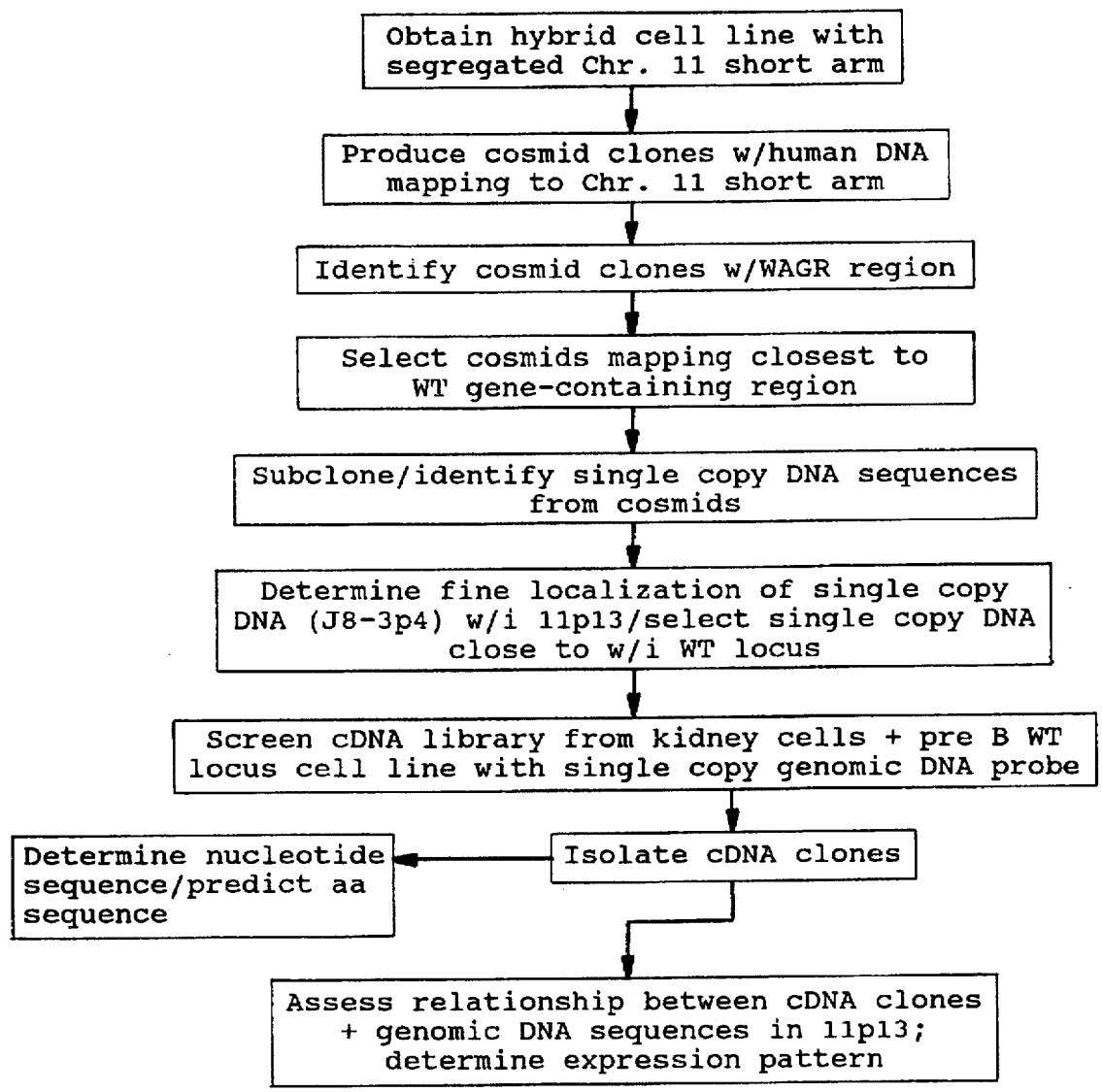
FIG. 1 is a schematic representation of isolation and characterization of the Wilms' tumor gene.

The present invention is based on the identification and characterization of the Wilms' tumor gene and the mRNA transcript of the gene, as well as on the characterization of the polypeptide encoded by the Wilms' tumor gene, and antibodies, both polyclonal and monoclonal, which react with (i.e., recognize) the polypeptide encoded by the Wilm's tumor gene. As described in detail below, a series of genomic and cDNA clones which map within the boundaries of constitutional and tumor deletions which define the Wilms' tumor locus on chromosome 11 band p13 (11p13) have been isolated and characterized (herein referred to as the WT1 gene). As also described below, the expression pattern of mRNA encoded by the transcription unit which corresponds to the clones has been determined. In addition, the polypeptide encoded by the Wilms' tumor locus has been characterized and shown to have several features which suggest it has a role in the regulation of transcription.

Based on the work described herein, methods of determining the presence or absence of the Wilms' tumor gene, the identification of mutations within the WT1 gene, as well as quantitating the WT1 gene product in cells, have been developed. Nucleic acid probes which hybridize to Wilms' tumor DNA and nucleic acid probes which hybridize to transcripts of the Wilms' tumor DNA have also been produced and used in the method. Although it is referred to herein as the Wilms' tumor gene or Wilms' tumor DNA, the locus on Chromosome 11 band 13 is referred to in this manner for convenience and is not meant to limit the present invention to the medical conditions designated WAGR and Wilms' tumor only. For example, it has recently been shown that mutations in the Wilms tumor suppressor gene (WT1) are associated with abnormal urogenital development in Denys-Drash syndrome. (Pelletier, J., et al., *Cell*, 67:437–447 (1991)). Thus, it is reasonable to expect that mutations of the WT1 gene occurs in (is associated with or causative of) other tumor types, such as leukemia cells and testicular tumors. The present invention is intended to include such an occurrence and provides a method by which the equivalent gene or DNA sequence (i.e., a DNA sequence which cross hybridizes with a probe as described herein and acts as a recessive oncogene or anti-oncogene in cells in which it occurs) can be identified in other types of tumors.

The following is a description of isolation and characterization of Wilms' tumor genomic DNA and cDNA, the mRNA transcripts, the encoded polypeptides and antibodies which recognize the encoded polypeptides.

Molecular mapping experiments have narrowed the WAGR regions to a specific interval in 11p13 bounded by the genes encoding erythrocyte catalase (CAT) and the subunit of follicle stimulating hormone (FSHB). Junien, et al., *Am. Genet.*, 23:16–168 (1980); van Heyningen, et al., *Proc. Natl. Acad. Sci. USA*, 82:8592–8596 (1985); Glaser, et al., *Nature*, 321:882–887 (2986); Proteous, et al., *Proc. Natl. Acad. Sci. USA*, 84:5355–5359 (1987); Watkins, et al., *DNA*, 6:205–212 (1987). Three complementary strategies have been used to further delineate the location of genes within the WAGR region: somatic cell genetics, molecular cloning and pulsed field gel electrophoresis. Somatic cell hybrids segregating specific translocation and deletion chromosomes have been valuable reagents for resolving and defining the position of individual genes within the WAGR region. A substantial number of additional 11p13 DNA markers have been isolated and characterized from chromosome 11-specific DNA libraries. Lewis, et al., ibid (1988); Compton, et al., *Cell*, 55:827–836 (1988); Davis, et al., *Genomics*, 3:24–27 (1988a); Davis, et al., *Science*, 241:840–842 (1988b); Gessler, et al., *J. Am. Hum. Genet.*, 44:486–495 (1989a); Gessler, et al., *Science*, 244:1575–1572 (1989b). Long range restriction maps constructed by pulsed field gel electrophoresis define relatively large intervals for several of the WAGR disease genes.

The method by which Wilms' tumor DNA was isolated is represented schematically in FIG. 1. Initially, a hamster-somatic human cell line (J1-11), in which the short arm of human chromosome 11 had been segregated from the remainder of the human genome, was used to produce cosmid libraries, as described in the Example. One hundred nineteen cosmid clones, all containing human DNA which mapped to the short arm of chromosome 11, were isolated from the library. Clones containing the WAGR region were subsequently identified, using a mapping panel of somatic cell hybrids containing different fragments of human chromosome 11p. Of the clones isolated in this manner, three (J7-18, J8-3 and J10-15) appeared to map most closely to the region containing the Wilms' tumor gene. The restriction maps of J8-3 and J10-15 showed substantial overlap and, therefore, only one of these cosmids (J8-3) was analyzed further.

Figure 2:
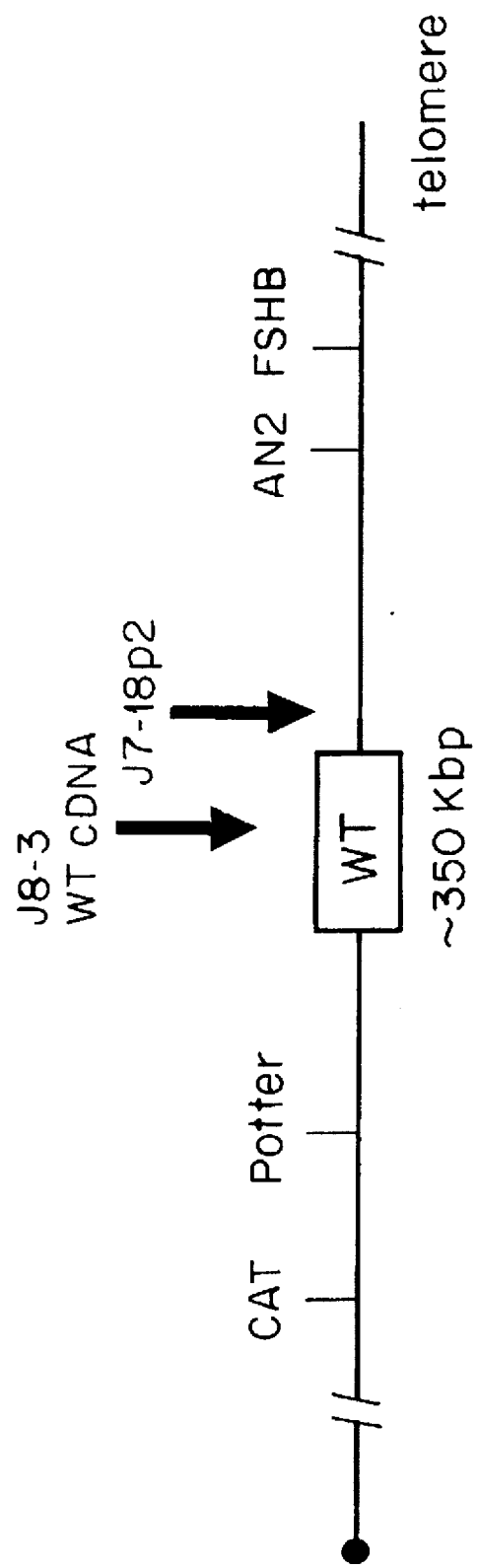
FIG. 2 is a schematic representation of the WAGR region showing the map positions of single copy probes J7-18p2, JS-3p4 and cDNAs homologous to J8-3.

Single copy sequences, designated J7-18p2 and J8-3p4, were subcloned and identified from cosmids J78-18 and J8-3, respectively. The fine localization of these single copy DNA sequences was determined by hybridization to a series of somatic cell hybrids derived from patients with translocations and deletions which define specific intervals within the WAGR region. This is described in detail in the Example and a map summarizing the findings is shown in FIG. 2.

JS-3p4 was used as a probe to screen cDNA libraries. JS-3p4 was selected for this purpose because its map position indicated that it was close to or within the Wilms' tumor locus. In addition, as explained in the Example, two observations suggested that J8-3p4 contained a portion of a transcription unit. A cDNA library derived from human embryonic kidney (HEK) cells was screened with JS-3p4. On the basis of Northern blotting results (as described in Example 1), a human adult kidney library and a human B cell library were also screened. Four cDNA clones from these three libraries were studied in detail: two from HEK (WT4, WT2), one from human adult kidney (WT22) and one from a pre B cell line (WT33). Another homologous cDNA clone (WT13) was isolated from the HEK library, using an independently isolated conserved genomic DNA clone, λK13. Glaser, T., the fine structure and evolution of the eleventh human chromosome. Ph.D. thesis, Massachusetts Institute of Technology, Cambridge, Mass. (1988).

cDNA clone WT33 is 2313 base pairs (bp) in length and the longest clone isolated. It extends the furthest in both the 5' and the 3' directions of the clones isolated. The other four cDNAs share a common internal region of DNA sequence approximately 1000 to 1200 bp in length.

cDNA clone WT33 was selected for further analysis, which is described in detail in Example 1. The WT33 nucleotide sequence was determined (SEQ ID NO: 1) and the predicted amino acid sequence was derived (SEQ ID NO: 2). Both are represented in FIG. 3. Sequence analysis showed the presence of a continuous open reading frame of 345 amino acids, which extends from nucleotides 1 to 1035. This open reading frame appears to represent most of the WT33 coding segment, but it does not appear to include the initiator methionine codon. Primer extension experiments suggested that an additional 700 bp were present at the 5' end of the mRNA corresponding to WT33. The transcription pattern of the locus corresponding to these cDNAs exhibits some complexity. Moreover, experiments utilizing RNA PCR (polymerase chain reaction) indicate variation in mRNA sequence in the 5' segment of the coding region of the mRNA, suggesting alternative splicing patterns among various tissue types.

Of particular interest is that nucleotides 670 to 1002 encode four contiguous "zinc finger" domains. All four zinc fingers encoded by WT33 (FIG. 5) fit the consensus sequence for zinc fingers (Miller, J., et al. *EMBO J.*, 4:1609–1614 (1985); Evans, R. N., et al., *Cell*, 52:1–3 (1988). The H/C link between zinc fingers, typified by the amino acid sequence TGE-R/K-P-F/Y-X, is also conserved in the deduced amino acid sequence. Shuh, R., et al., *Cell*, 47:1025–1032 (1986).

A search of other polypeptides for sequences related to WT33 revealed a 51% similarity between the amino acid sequence of the zinc finger region of two recently identified human early growth response genes, EGR1, Sukhatme, et al., *Cell*, 53:37–43 (1988) and EGR2, Joseph, et al., *Proc. Natl. Acad. Sci. USA*, 85:7164–7168 (1988). The early growth response genes have been suggested to be involved in pathways controlling cell proliferation. The individual zinc fingers of WT33 are aligned with the zinc finger consensus sequence and compared with the zinc fingers of EGR1 and EGR2 in FIG. 5. Although the WT33 polypeptide has homology to zinc fingers in other proteins, including TFIIIA and Sp1, the degree of homology is greatest with EGR1 and EGR2 and moreover was observed throughout all three contiguous zinc fingers.

The amino acid content of the region 5' amino terminal to the zinc finger domain is also characteristic of proteins thought to be transcription factors. From the amino terminus to the start of the first zinc finger, there is a high concentration of serine (10.2%), proline (9.8%), glycine (9.7%), threonine (8.8%) and glutamine (7.9%) residues. These amino acids are also highly represented in the amino termini of the polypeptides encoded by EGR1 and EGR2. Proline and glutamine rich domains have been identified as motifs in a number of transcription factors and putative transcription factors. Mitchell and Tjian, *Science*, 245:371–378 (1989). A high threonine and serine content is also observed in several transcription factors, including Sp1. Courey, et al., *Cell*, 55:887–898 (1988).

Figure 6A:
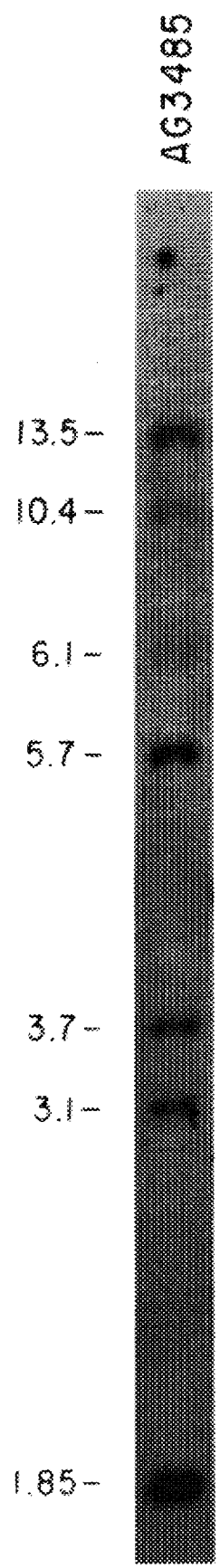
FIGS. 6A and 6B shows the results of Southern blot analysis of EcoRI digested human lymphoblast DNA hybridized with WT33.
Figure 6B:
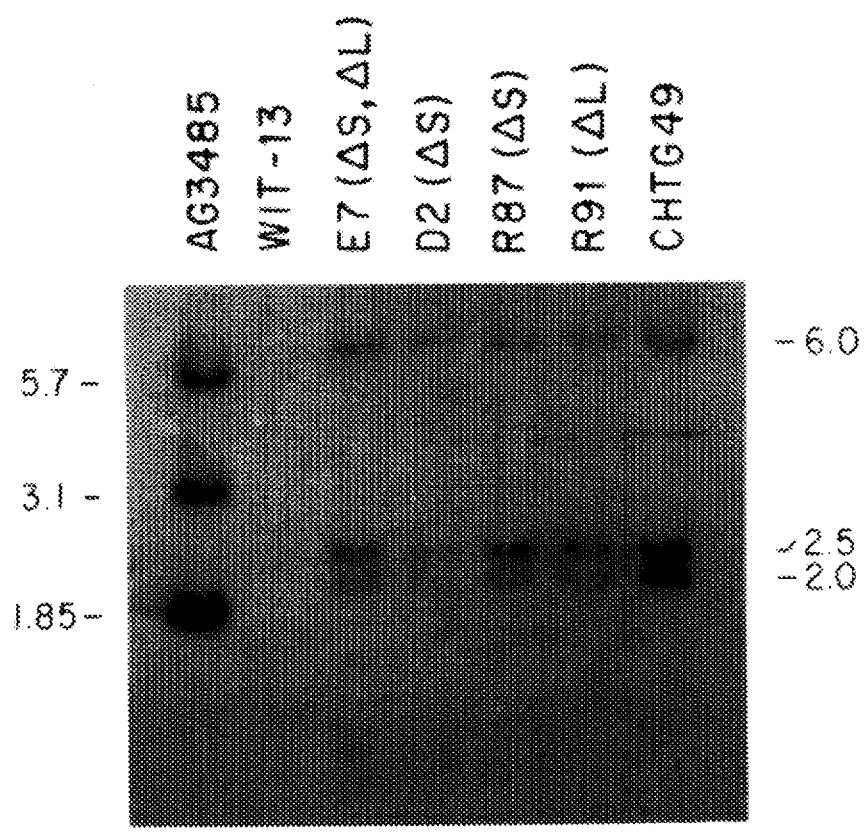

The relationship between cDNA clones isolated as described and genomic DNA sequences in 11p13 was also addressed, as described in detail in Example 1. Briefly, segments of the WT33 cDNA were hybridized to genomic DNA from diploid human cell lines and to a panel of somatic cell hybrids which permits fine structure mapping within 11p13 (Table). As shown in FIG. 6A, WT33 hybridizes to seven EcoRI fragments in normal human DNA which are 13.5, 10.4, 6.1, 5.7, 3.1, and 1.85 kb in length. Analysis of somatic cell hybrids confirmed that all of these restriction fragments are located on chromosome 11 in band p13. Furthermore, these DNA sequences are all homozygously deleted no cell line WIT-13 and hybrids derived from this line. (FIG. 6B and data not shown).

Figure 7:
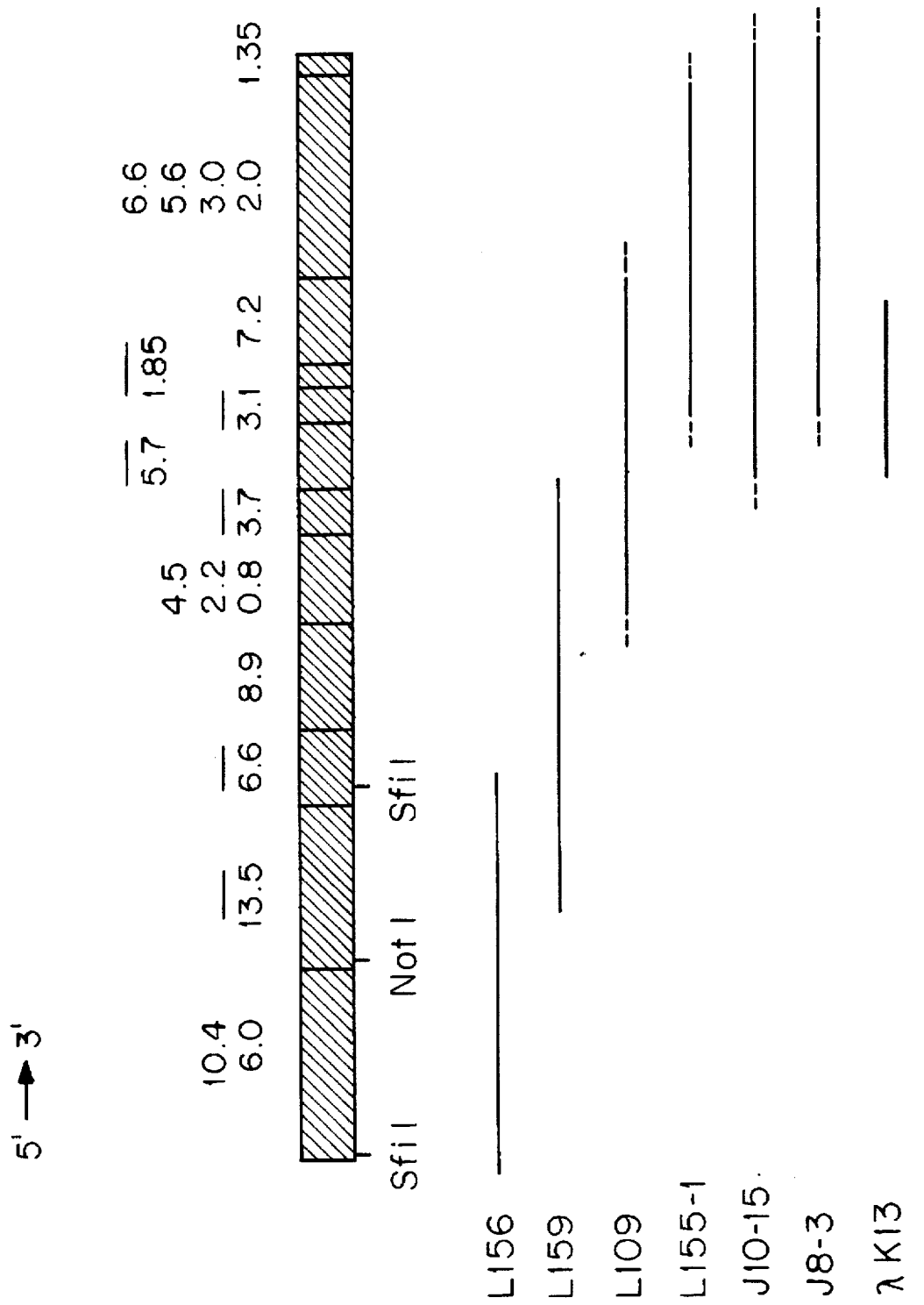
FIG. 7 shows the genomic organization of six overlapping cosmids encoding the WT33 mRNA; a composite EcoRI restriction map of the 93 Kbp genomic region spanning the WT33 cDNA is shown at the top of the Figure.

To further analyze the structure of the genomic DNA within the region, WT33 was used as a probe to isolate additional cosmid DNA clones. FIG. 7 shows a composite map of four cosmids derived from this analysis (L156, L159, L109, L155-1) plus the two original cosmids, J8-3 and J10-15, and phage clone λK13. (Glaser, T., The fine structure and evolution of the eleventh human chromosome. Ph.D. thesis, Massachusetts Institute of Technology, Cambridge, Mass. (1988)). The cloned genomic sequences span a DNA segment greater than 90 kb in length. To relate genomic and cDNA clones, an Eco RI digest of each cosmid was hybridized with segments of WT33 cDNA. In this manner, all seven Eco RI fragments observed by Southern hybridization of the cDNA to genomic DNA were identified within the collection of overlapping clones (FIG. 7). Orientation of the transcriptional unit was established by hybridizing restriction digests of each cosmid with probes derived from different subregions of the WT33 cDNA. (See Example 1). These data indicate that the WT33 transcriptional unit must extend from a position close to the Not I site in cosmid L156 and continue in the 3′ direction, extending through the 1.85 kb Eco RI fragment common to cosmids L109, L155-1, J10-15, J8-3 and clone λK13. These hybridizing Eco RI fragments span approximately 50 kb.

In analysis of restriction enzyme recognition sites in cloned genomic DNA permits a direct comparison to the pulsed field gel electrophoresis map of the region. As shown in FIG. 7, the 5′ end of the genomic DNA segment encoding the 5′ end of WT33 cDNA includes a recognition site for the restriction enzyme Not I. Pulsed field gel mapping demonstrates that the 11p13 Wilms' tumor gene is located within the boundaries of two adjacent Not I fragments, 500 kb and 325 kb in length. Hybridization to genomic DNA digested with both Sfi I and Not I confirms that the Not I site in cosmid L156 represents the junction between the 325 kb and 500 kb Not I restriction fragments. Since pulsed field gel analysis places the 500 kb Not I fragment centromeric to the 325 kb Not I fragment, transcription must proceed in a centromeric to telomeric direction.

Cosmid L156 contains sites for a number of restriction enzymes with recognition sequences which contain the dinucleotide CpG, including Not I, BssH II and Eag I. These data, as well as pulsed field gel analysis, indicate the presence of an "HTF island" in the region of genomic DNA surrounding the Not I site. HTF islands are frequently located at the 5′ ends of transcription units. Bird, A., et al., *Cell*, 40:91–99 (1985); Bird, A., *Nature*, 321:209–213 (1986); Lindsay, S., et al., *Nature*, 327:336 (1987), suggesting that the genomic DNA in cosmid L156 may contain the 5′ end of the WT33 transcription unit.

Figure 8A:
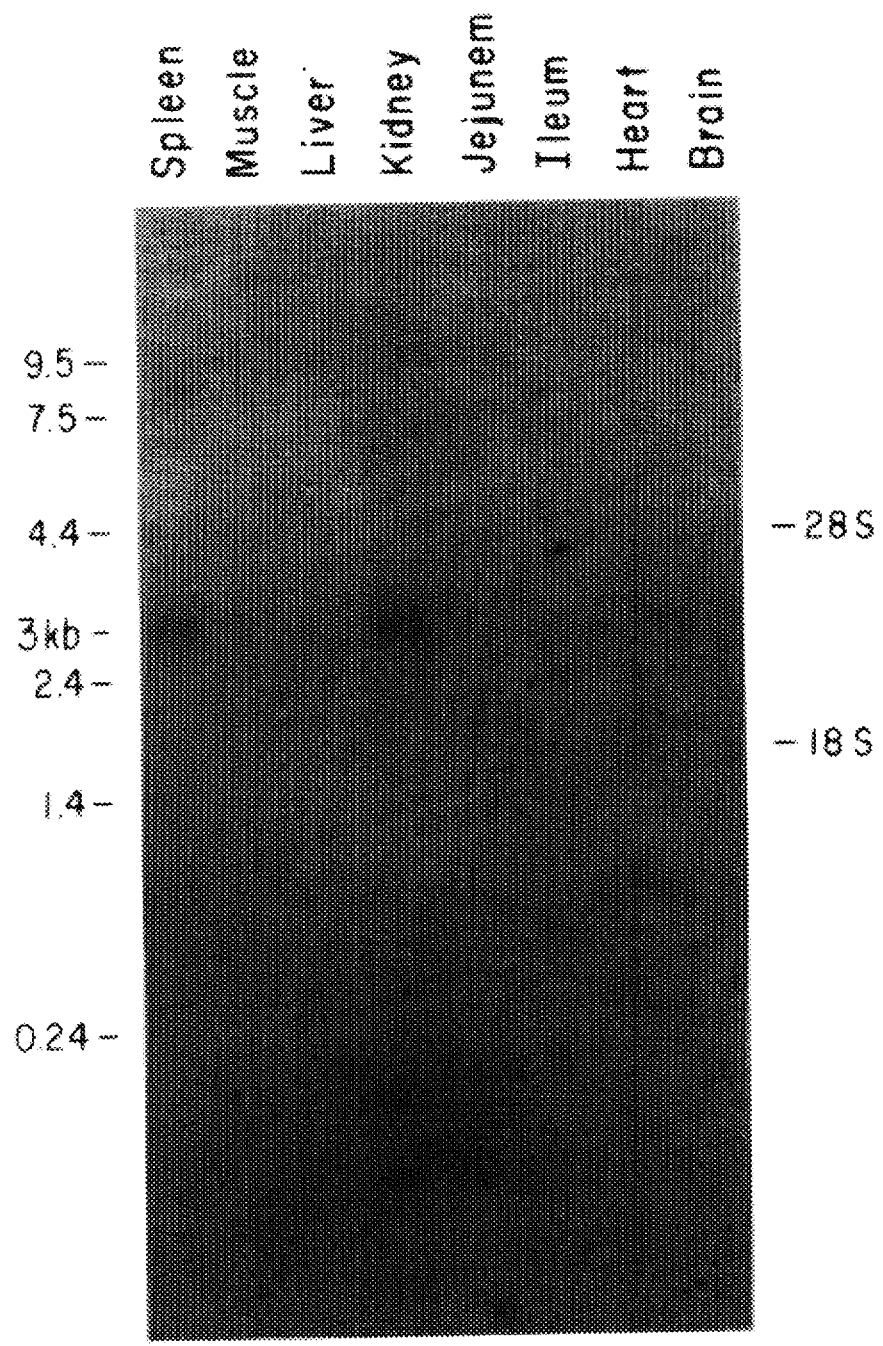
FIG. 8A shows the results of Northern blot analysis of the tissue specific expression of WT33 in baboon.
Figure 8B:
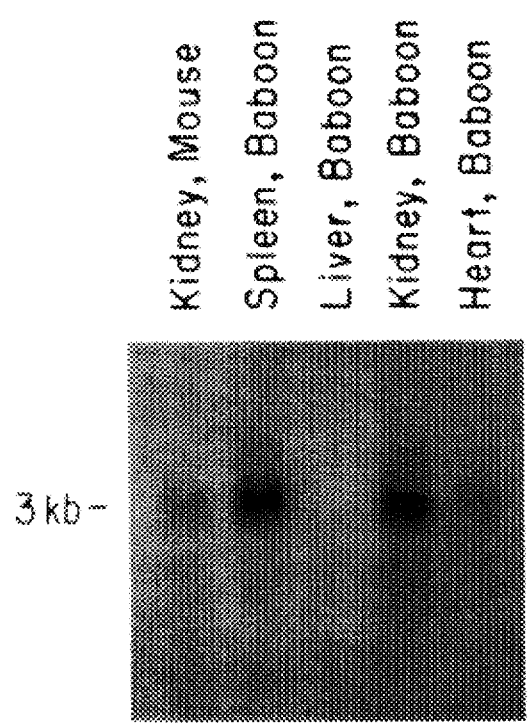
FIG. 8B shows the results of Northern blot analysis of the tissue specific distribution of RNA from mouse and baboon tissues.

The size and tissue distribution of the WT33 transcript (2), were also assessed, by performing a series of Northern blotting experiments. FIG. 8A shows the hybridization of WT33 cDNA to total cellular RNA isolated from a variety of baboon tissues. A mRNA species approximately 3 kb in length is detected in baboon kidney and spleen RNA. A faint hybridization band at 3 kb is also observed in heart upon long exposure (FIG. 8B), while no detectable hybridization is observed in RNA derived from muscle, liver, jejunum, ileum or brain (FIG. 8A). WT33 is an effective probe in hybridization to RNA derived from mouse tissues as well. A 3 kb mRNA species homologous to WT33 is observed in mouse tissue as well. A 3 kbmRNA species homologous to WT33 is observed in mouse kidney (FIG. 8B). The tissue specific expression pattern of WT33 mRNA in the adult mouse is similar to the baboon. Developmental studies in the mouse show that the WT33 mRNA is most highly expressed in fetal kidney. This expression is consistent with a gene capable of growth regulation in the metanephric blastema, the presumed tissue of origin for Wilms' tumor. Bove, et al., (1976) ibid. The finding of homology with the EGR1 and EGR2 genes also suggests WT33 may exert a role in the growth regulation of nephroblasts.

Figure 8C:
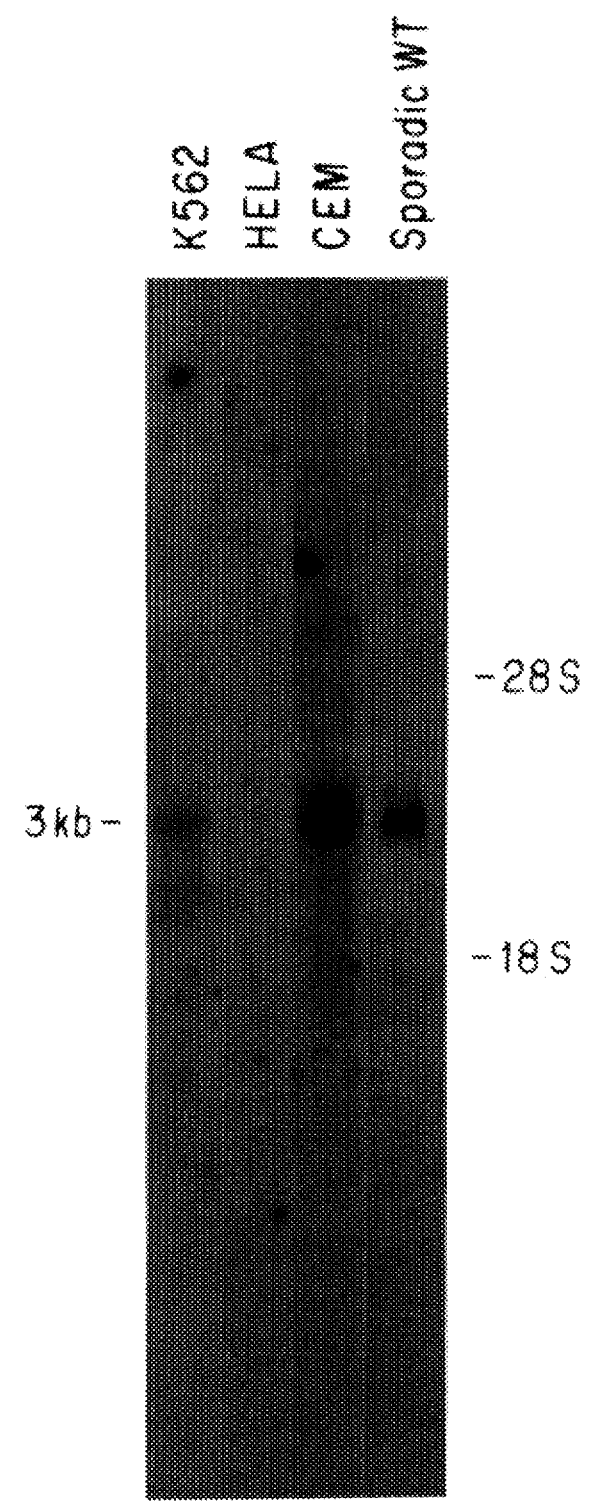
FIG. 8C shows the results of Northern blot analysis of expression of WT33 in tumor cell lines.

A spectrum of tumor cell lines, including two neuroblastomas (SK-N-Be(2) and NGP), a retinoblastoma (WERI) a breast carcinoma (MCF7), two osteosarcomas (HOS and U205), two melanomas (SK-MEL-130 and SK-MEL-147), a bladder carcinoma (Ej), two colon carcinomas (SE480 and WIDR), a cervical carcinoma (HeLa) and two Esptein-Barr virus transformed B cell lines (TSH-1 and TSH-2) did not show detectable hybridization to WT33 cDNA. In contrast, RNA isolated from several sporadic Wilms' tumors showed strong hybridization to WT33 cDNA at the 3 kb position. An example is shown in FIG. 8C. Similarly, RNA isolated from two hematopoietic cell lines, an erythroleukemia (K562) and an acute lymphocytic leukemia (CEM), also showed strong hybridization to WT33 at the 3 kb position (FIG. 8C). Results demonstrated expression of the WT33 transcript in cells of kidney and a subset of hematopoietic cell lines. These results are consistent with the tissue-specific expression observed predominantly in the baboon kidney and spleen.

In order to study in detail the developmental expression of Wilms' tumor DNA, the mouse homolog of the human gene was isolated as described in Buckler, A. J., et al., *Mol. Cell. Biol.*, 11:1708–1712 (1991), the teachings of which are herein incorporated by reference. The complete nucleotide sequence of the murine WT1 cDNAs (3,089 bp) is shown in FIG. 9A and 9B (SEQ ID NO: 3) along with its predicted amino acid sequence (SEQ ID NO: 4). A long open reading frame (ORF) was observed, extending from nucleotide 106 to a stop codon at position 1825. An ATG at position 478 predicts a polypeptide product of 449 amino acids, having a molecular mass of approximately 50 kDa. A small ORF exists upstream of this translation start site (nucleotides 8 to 67)). Sequence extension (at the 5′ end) by RNA-based polymerase chain reaction reveals termination codons in all three reading frames upstream of this small ORF. (Pelletier, J., et al., *Genes & Develop.*, 5:1345–1356 (1991)). The predicted polypeptides of the human (SEQ ID NO: 6) and mouse cDNAs (SEQ ID NO: 4) show striking amino acid sequence identity (>96%; FIG. 10). The amino acid differences between the species occur primarily in the non-zinc finger regions of the polypeptide and, interestingly, are not conservative changes.

The overall nucleotide sequence homology between the murine and human cDNAs is approximately 81%. An extremely high degree of homology exists within the protein-encoding region (91%) and is most pronounced in the region comprising the zinc finger domains (95%). Significant homology also exists within the 5' and 3' untranslated regions (79 and 73%, respectively), suggesting that conserved sequences in these areas also may be functionally important.

The WT1 gene contains ten exons which encode four distinct mRNA species, reflecting the presence or absence of two alternatively spliced transcripts. The transcript containing both alternative splices is the most prevalent variant, whereas the least common is the one missing both alternatively spliced exons. The relative level of each isoforms is constant during the development, as well as Wilms' tumor. (Haber, D. A., et al., *Proc. Natl. Acad. Sci. USA* 88:9618–9622 (1991)). Two of the four WT1 isoforms differ in DNA binding capacity (Rauscher F. J., et al., *Science*, 1259–1261 (1990)).

The predicted WT1 protein (SEQ ID NO: 4) shows several features of a transcription factor, including four Cys2-His2 zinc fingers at the carboxy terminus. WT1 can bind to DNA sequences similar to those recognized by the early growth response genes (EGR) and there is evidence that WT1 regulates the expression of insulin-like growth factor (IFG2) (Drummond, I. A., et al., *Science* 257:674–677 (1992)) and platelet-derived growth factor alpha (PDGFA) (Gashler, A. L., et al., *Proc. Natl. Acad. Sci. USA* 89:10984–10988 (1992)) and, thus, may directly be involved in regulating cellular differentiation and proliferation.

The relative abundance of the different WT1 splice forms is similar among various mouse and human tissues, as well as among different Wilms' tumors. The various splice forms are referred to as A, which lacks both alternatively spliced exons; B, which contains the first alternatively spliced exon; C, which contains the second alternatively spliced exon; and D, which contains both alternatively chosen exons. (Haber, D. A., et al., *Proc. Natl. Acad. Sci. USA*, 88:9618–9622 (1991)).

A plasmid expressing a glutathione S-transferase (GST) Wilms' Tumor WT33 fusion protein was generated as described in detail in Example 2. The plasmid is capable of expressing the WT33 gene product (SEQ ID NO: 2). A plasmid expressing a glutathione S-transferase Wilms' Tumor WT1 fusion protein was also generated in the same manner as the WT33 fusion protein, also as described in Example 2.

Figure 11:
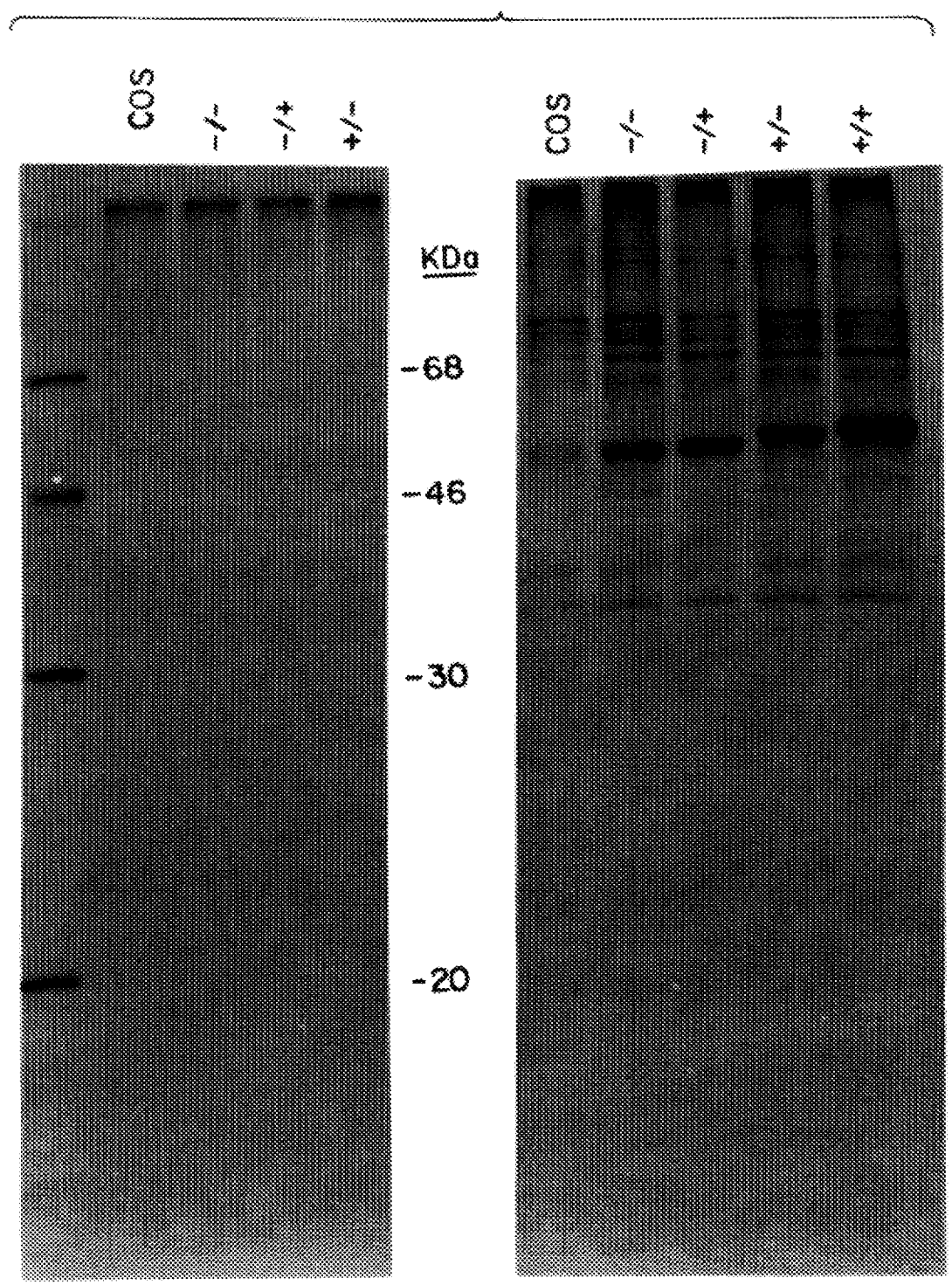
FIG. 11 shows the immunoprecipitation of the WT1 polypeptide using anti-WT1 polyclonal antibodies.

Polyclonal and monoclonal antibodies have been generated which recognize the WT1 polypeptide. As described in Example 3, polyclonal antibodies were produced by immunizing rabbits with WT1-GST fusion protein, following standard laboratory procedures. Example 3 also demonstrates the reactivity of the WT1 polyclonal antibody by immunoprecipitation experiments (FIG. 11).

Figure 12:
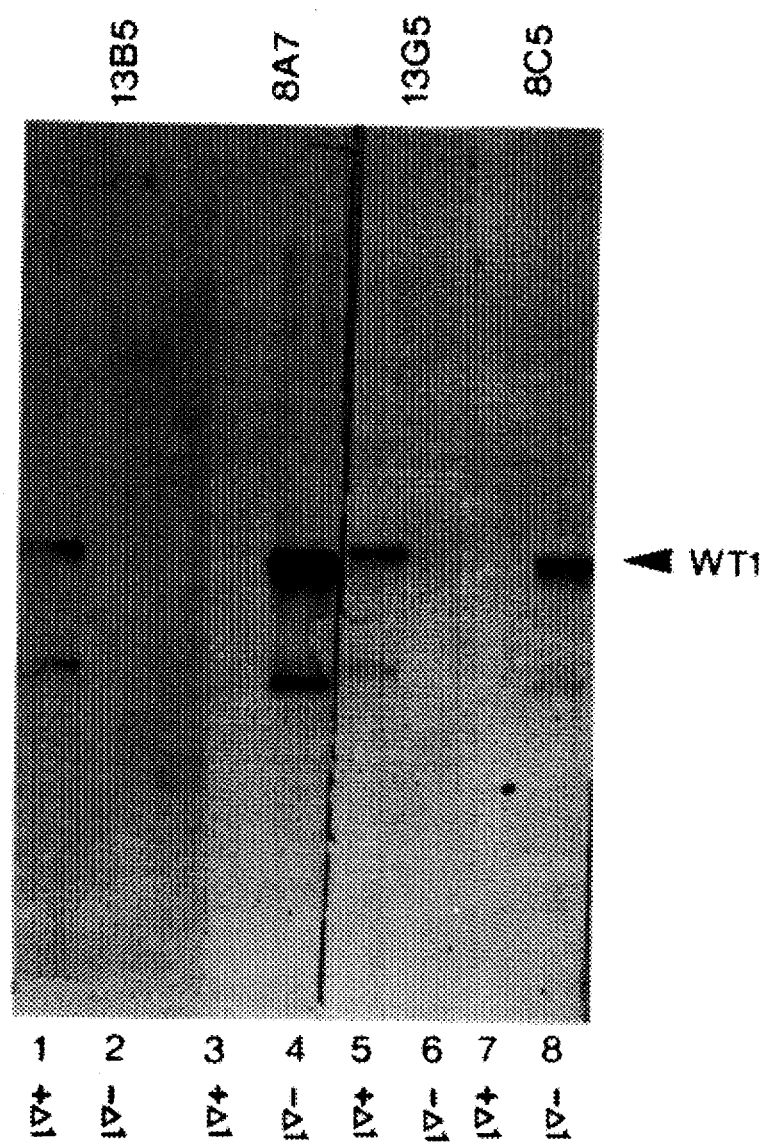
FIG. 12 shows the Western blot characterization of monoclonal antibodies against the WT1 polypeptide, specific to the first alternative splice site.

Example 4 describes in detail, the generation of monoclonal antibodies against WT1 gene product. Peptides specific to the first alternative splice site of WT1 were used following standard laboratory procedures to produce hybridomas which recognize the WT1 polypeptide (FIG. 12).

Thus, as described above, DNA which corresponds to the Wilms' tumor gene (SEQ ID NOS: 1 and 3) was identified, isolated and sequenced. The DNA has been shown to encode a transcription unit which spans approximately 50 kb and encodes an mRNA approximately 3 kb in length. This mRNA is expressed in various tissues, but predominantly in kidney, and male and female gonadal tissue. The WT1 predicted polypeptides encoded by this locus have a number of features which suggest a potential role in the regulation of transcription. These include the presence of four zinc finger domains and a region rich in proline glutamine (SEQ ID NO: 5). The amino acid sequences of the predicted polypeptides show significant homology to two growth regulated mammalian polypeptides EGR1 and EGR2. The genetic localization of this gene, its tissue-specific expression, and the function predicted from its sequence indicate that it represents the 11p13 Wilms' tumor gene.

The Wilms' tumor suppressor gene, herein referred to as WT1, has four alternately spliced mRNA transcripts, reflecting the presence, or absence of two differentially spliced exons in the coding region of the WT1 mRNA. That is, translation of the four WT1 transcripts results in four distinct polypeptides. All four WT1 isoforms contain four $Cys_2$-$His_5$ zinc fingers, with two of the four isoforms differing in DNA binding specificity.

The relative abundance of the different WT1 splice forms is similar among various mouse and human tissues. However, recent results raise the possibility that cellular control of the WT1 activity involves modulation of the ratio of WT1 isoforms. Thus, for example, a mutation (i.e., deletion or addition) in one of the WT1 isoforms leads to a disruption of the ratio of isoforms normally present (e.g., a decrease in production of some of the isoforms will disrupt the ratio). A detection of a mutation in a WT1 isoform leading to a deruption of the isoform ratio, is indicative of a predisposition to developing a Wilm's tumor malignancy or other urogenital malformation (Breuning, W., et al., *Nature Genetics*, 1:144–148 (1992)). If a WT1 isoform is mutated, the gene product will not bind properly to DNA and therefore will not suppress subsequent gene activity (e.g., regulation of the EGR genes).

A genetic predisposition of Wilms' tumor has been reported in two disease syndromes, WAGR and Denys-Drash. (Pelletier, J., et al., *Cell*, 67:437–447 (1991)). For example, studies indicate that 40–60% of individuals with the WAGR syndrome go on to develop Wilms' tumors. However, additional analyses in patients with Wilms' tumors suggest that the genetic factors involved may be more complex. Patients with a familial symptom complex involving Wilms' tumor, aniridia, genitourinary abnormalities, and mental retardation (so-called WAGR syndrome) show constitutional chromosome deletions that include 11p13. Analysis of sporadic tumors has also demonstrated reduction to homozygosity at loci within 11p13, a pattern analogous to that of retinoblastoma. However, a minority of sporadic tumors and patients with Wilms' tumors arising in the context of the Beckwith-Wiedemann syndrome show loss of heterozygosity not at 11p13, but at 11p15. Further studies have also identified some familial Wilms' tumors in which linkage analysis excludes both 11p13 and 11p15, suggesting a possible third locus involved in this tumor. (Haber, D. A., et al., *Cell* 61:1257–1269 (1990)).

As a result of the isolation and characterization of the Wilms' tumor gene, the nucleic acid sequence is available, as are other reagents (e.g., nucleic acid probes, antibodies) useful in a number of methods. These methods can be used for diagnostic purposes, such as in assessing the predisposition (i.e., likelihood/risk) of development of Wilms' tumor. For example, a biological sample obtained from an individual (e.g., kidney tissue) can be probed with all or a portion of the nucleotide sequence represented in FIG. 3 or FIG. 9A and 9B, using known techniques. The nucleotide sequence of such a probe need not be precisely the same as that in the Figures. It need be only sufficiently similar to the sequence that it will hybridize to the Wilms' tumor gene under the conditions used. A biological sample (e.g., blood cell or kidney tissue) can be obtained prenatally or postnatally and the occurrence of the Wilms' tumor gene assessed. Cells can be analyzed for the Wilms' tumor DNA, the encoded RNA transcripts (e.g., any one of the four isoforms) and/or polypeptides encoded by the Wilms' tumor gene. This can be carried out using standard blotting techhiques, (e.g., Southern blot)and a radioactively labelled DNA probe which hybridizes to (is complementary to) all or a portion of the Wilms' tumor. A radioactively-labelled DNA probe can be combined with cellular DNA previously treated to render it available for hybridization with complementary DNA, under conditions appropriate for hybridization to occur. After sufficient time for the labelled DNA probe and the complementary DNA in the sample (if present) to hybridize and form labelled DNA probe/sample DNA complexes, detection of the labelled probe/sample DNA complexes is carried out using known methods (e.g., autoradiography). The label can be any substance which can be detected and whose presence does not interfere with the availability to probe DNA to bind to complementary DNA (e.g., fluorescent material). The method by which labelled DNA probe/sample DNA complexes are detected will depend on the type of label used (e.g., in the case in which a fluorophore is used, fluorescence detection will be used).

If necessary, DNA obtained from the sample can be amplified, using a known technique such as the polymerase chain reaction, and the amplified DNA analyzed for the occurrence of Wilms' tumor DNA or mutations in Wilms' tumor DNA as taught in Pelletier, J., et al., *Nature*, 353:431–434 (1991), and Haber, D. A., et al., *Proc. Natl. Acad. Sci. USA* 88:9618–9622 (1991), the teachings of which are herein incorporated by reference. If sample DNA is amplified, the product is an amplification mixture which contains amplified DNA of interest (DNA which includes Wilms' tumor DNA) and amplified DNA other than DNA of interest. Generally, DNA in the amplification mixture is separated on the basis of size, using known techniques. Chemical detection methods can also be used. The separated amplified DNA is analyzed for DNA of interest using a known technique, such as Southern blotting, DNA sequencing, digestion with appropriate restriction endonuclease or visualization of ethidium bromide stained gels.

Alternatively, mRNA can be detected in the sample obtained, using as a probe all or a portion of the Wilms' tumor gene. This can be carried out using mRNA obtained from an individual's cells, or using mRNA obtained from cells and amplified using a known amplification technique, such as the RNA PCR. In either case, RNA is analyzed using a known technique, such as Northern blotting.

Antibodies specific for the Wilms' tumor gene-encoded protein (SEQ ID NOS: 2 and 4) (or a polypeptide portion) can also be used for diagnostic purposes. Such antibodies can be produced by the protocols as described in Examples 3 and 4 or by using known techniques, such as described in Ausubel, et al., *Current Protocols in Molecular Biology*, Greene Publishing Associates and Wiley-Interscience 1989).

The resultant antibodies (both polyclonal and monoclonal) can then be used as probes in the assay methods described herein. Such antibody probes are particularly sensitive to alterations (i.e., deletions, or additions) in a suppressor gene, which affect the resultant protein products. Thus, the antibody probes provide a Simple and efficient means of determining whether a mutation of the gene has affected a functional unit. By using antibody probes it is possible to determine both the level of expressed protein and whether there has been a change in expression. One can compare results against base line levels obtained for the biological sample being tested (e.g., level of suppressor gene product in kidney tissue) by comparing biological material from the individual to be tested (i.e., patient) with tissue from another individual, who does not show symptoms of Wilms' tumor. If there is a change (e.g., absence of, or presence of, a reactive protein of altered electrophoretic mobility) it is indicative that the patient is predisposed to Wilms' tumor. Further, one can take test samples from the same individual at various times to provide levels of comparison.

In accordance with this invention, an antibody or cocktail of probes, e.g., antibody probes, can be used for detection. The probes, e.g., antibodies, can be labelled directly with a reporter or indirectly with a member of a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3(dimethylaminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which posses different functional groups. The most common commercially available heterobifunctional crosslinkers have an amine reactive N-hydroxysuccinimide ester as one functional group, and a sulfdhydryl reactive group as the second functional group. The most common sulfhydryl reactive groups are maleimides, pyridyl disulfides and active halogens. One of the functional groups can be a photoactive aryl nitrene, which upon groups can be a photoactive aryl nitrene, which upon irradiation reacts with a variety of groups.

The detectably-labelled probe, e.g., antibody detectably-labelled antibodies, or detectably-labelled member of the specific binding pair is coupled to a reporter which can be radioactive isotope, enzyme, fluorogenic, chemiluminescent or electrochemical materials. Two commonly used radioactive isotopic labeling procedures include the chloramine T, lactoperoxidase and Bolton-Hunter methods for $^{125}$I and reduction methylation for $^3$H.

Enzymes suitable for use in this invention include, but are not linked to, horseradish peroxidase, alkaline phosphate, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlman, *Immunochemistry* 8:871-(1971), Avrameas and Ternynck, *Immunochemistry* 8:1175 (1975, Ishikawa, et al., *J. Immunochemistry* 4:(3):209-327 (1983) and Jablonski, *Anal. Biochem.* 148:199 (1985).

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody to detect can be detectably-labelled directly with a reporter or indirectly with a first member of a specific binding pair. When the antibody is coupled to a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is a sandwich assay in which the capture reagent has been immobilized, using conventional techniques, on the surface of a support. For example, polyclonal or one, or more monoclonal antibodies to the WT1 protein, produced as described herein, are immobilized on a solid support.

Suitable supports used in assays include synthetic polymer supports, such as polypropylene, polystyrene, substituted polystyrene, e.g., aminated or carboxylated polystyrene, polyacrylamides, polyamides, polyvinylchloride, glass beads, agarose, or nitrocellulose.

In one embodiment, a suitably prepared biological sample is reacted with the antibody. Subsequently, an antibody specific for the polypeptide encoded by the Wilms' tumor gene (e.g., as shown in SEQ ID NOS 2 and 4, or their functional equivalents) are. The antibody used can be detectably labeled (e.g., with a radioactive or fluorescent material). After sufficient time for polypeptide present in the sample and antibody to combine or bind, to form Wilms' tumor gene-encoded polypeptide/specific antibody complexes, the occurrence (presence or absence and/or quantity) of complexes is determined, using known techniques. If labelled specific antibody is used, the occurrence of labelled complexes is determined (e.g., by autoradiography, fluorescence detection).

Alternatively, the sample can be combined with a solid support (e.g., nitrocellulose, glass slide, polystyrene beads, immunomagnetic beads) which bears an antibody specific for the antibody present in the complex. This results in binding of specific antibody in the sample (e.g., in the polypeptide/specific antibody complex) to the solid support. The resulting solid support-bound complex can be removed from the sample and detected using known techniques. For example, if the antibody in the Wilms' tumor gene-encoded polypeptide/specific antibody complex is labelled, detection of the support-bound complex is carried out by detecting the label.

Detection of mutated WT1 proteins can also be accomplished by quantitative Western blot analysis, as described in Example 5, using a commercially available kit such as the ECL Western Blot Detection Kit (Amersham, Inc.) For example, a biological sample, such as kidney tissue which is expected to contain the WT1 protein, is suitably prepared for SDS/polyacrylamide gel electrophoresis. A control sample (i.e., a biological sample obtained from a similar tissue source, known to have normal, or non-mutated WT1 protein) is run in parallel with the test biological sample (i.e., a sample of tissue from an individual to be tested for the presence of mutated WT1). Normal, or non-mutated WT1 protein is defined herein as having the normal ratio of four WT1 isoforms. Alternately, a control sample can be obtained from cell lines expressing the WT1 isoforms in a normal ratio.

The four WT1 isoforms of the WT1 gene produce four distinct polypeptides proteins that migrate as separate bands on an SDS/polyacrylamide gel. If the ratio of the four WT1 isoforms is normal (i.e., unaltered, with no mutation in the WT1 gene) then a normal amount of (quantity of) the resulting proteins are produced, which migrate as two distinct bands on SDS/PAGE. If the ratio of the four WT1 isoforms is abnormal (i.e., altered indicating a mutation in the WT1 gene), then the quantity of the resulting proteins is also altered. If a control sample, representing the unaltered WT1 gene is assayed in parellel with the test sample on a polyacrylamide gel and the resulting protein bands electrotransferred to a membrane, reacted (i.e., contacted with) the antibodies described herein (either polyclonal or monoclonal) and quantitatively visualized (e.g., by a second antibody such as anti-IgG, which is detectably labeled with a radioactive tag or chemiluminescent tag or $^{125}$I-labeled Protein A), the amount of the visualized, or quantitatied protein in their respective bands is indicative of the ratio of WT1 isoforms, which in turn, is indicative of a mutation of the WT1 gene.

Alternately, if there is a mutation in the WT1 gene resulting in an altered ratio of WT1 isoforms, the mutation may be such that the mobility of the resulting polypeptides will be altered (i.e., of the polypeptide is shorter or longer than the unaltered polypeptide). In this case, the polypeptide will migrate with altered mobility in the SDS/PAGE and the resulting protein (if it is recognized by the anti-WT1 antibody) will be visualized at a different location in the gel, thus, again indicating an altered ratio of isoforms and a mutation in the WT1 gene.

The above probes (e.g., DNA probes, mRNA probes and antibody probes) are used to determine alterations in the Wilms' tumor gene in individuals. These alterations can be the aforementioned mutations (e.g., deletions, additions or substitutions) in the WT1 gene. One preferred portion of the gene to look at is that encoding the zinc finger regions or their expression product, preferably the nucleotides coding for at least one of the zinc finger regions; the antibody probe detects affinity with the residue itself. The probes are to the entire gene shown in FIG. 3, FIG. 9A and 9B or portions thereof. As known in the art, such portions should be at least about 20 nucleotides in length. In one preferred embodiment, a probe serves as at least one of the primers for a PCR to determine mutations in the gene by looking at the DNA or mRNA, as described in Breuning, W., et al., *Nature Genetics*, 1:144-148 (1992). The detection of such a deletion or alteration of a functional portion is indicative of a cancerous or precancerous condition. For example, taking a predetermined cell or fluid sample from a human, adding the probe to the cell or fluid sample and determining from the probe whether there has been an alteration or deletion of a function portion of the WT1 gene or gene product, wherein such an alteration or deletion is indicative of the cancerous or precancerous condition. Standard techniques such as Southern blot, Northern blot, Ligase chain reaction (LCR) PCR, ELISA, immunoassay can be used to make the determination.

The present method is useful for early detection of cancer and precancerous conditions. The present method is particularly useful to diagnose a predisposition to Wilms' tumor, as seen in WAGR and Denys-Drash, and, as a result, earlier intervention, in the form of surgery, chemotherapy and/or radiation therapy, will be possible. For example, the present method can be used to evaluate a patient presenting with an enlarging abdominal mass, abdominal pain, hematuria or constitutional symptoms (e.g., fever, vomiting, poor appetite, malaise, polycythemia, hypertension) which is suggestive of Wilms' tumor. That individual can, after diagnosis through use of the present method, be treated as described.

The present method of detecting the Wilms' tumor gene and gene products can also be used to identify in other tumor types a lesion which is the same as or similar to the lesions which occur in the case of Wilms' tumor. It is important to note that the WT1 protein has been detected in a variety of developing and adult human tissues, as described in Example 5.

Figure 13:
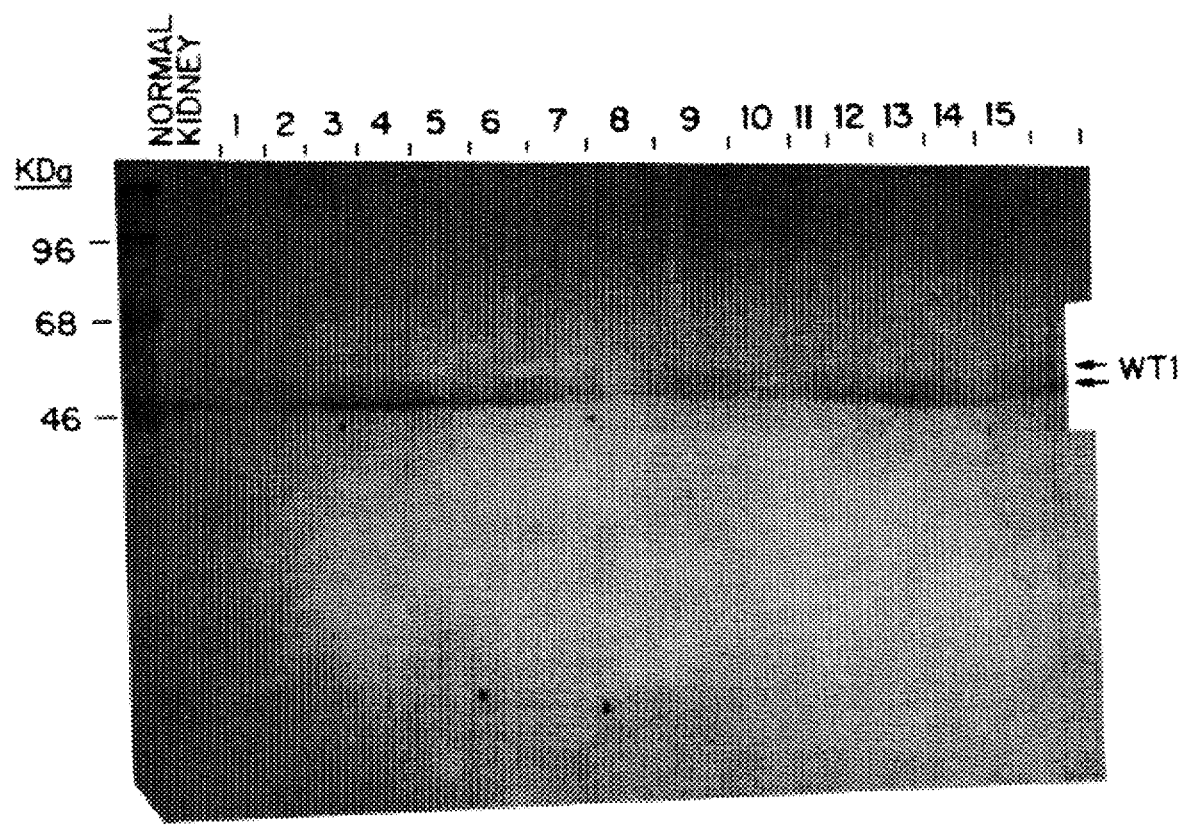
FIG. 13 shows detection of a polypeptide in protein extracts from Wilms' tumors using polyclonal anti-WT1 antibodies.
Figure 14A:
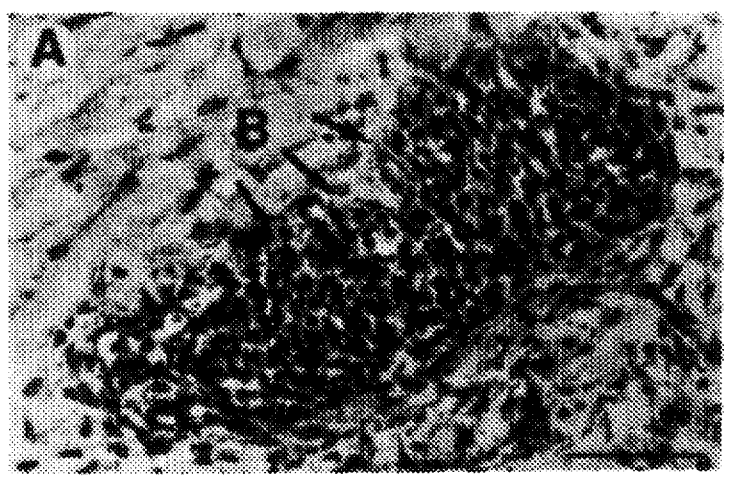
FIGS. 14A–14E shows WT1 expression in Wilm's tumor. Immunofluorescence shows nuclear staining (FIG. 14B) in blasterma and (FIG. 14D) glomeruloid structures. Bright light images show blastema (FIG. 14A) and glomeruloid structures (FIG. 14C), confocal microscopy phase contrast overlay (FIG. 14E).
Figure 14B:
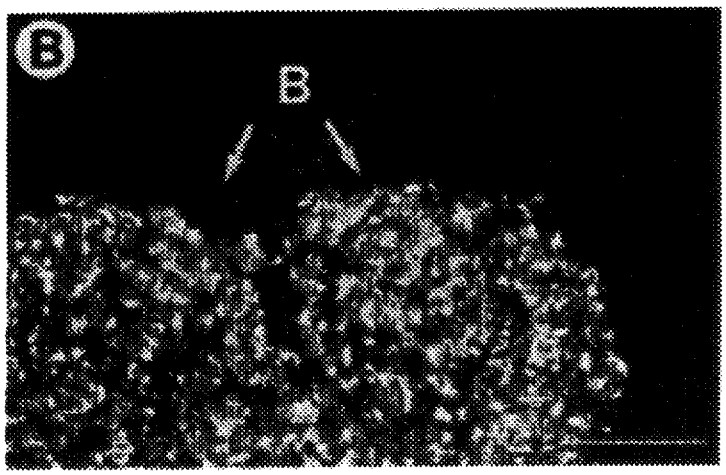
Figure 14C:
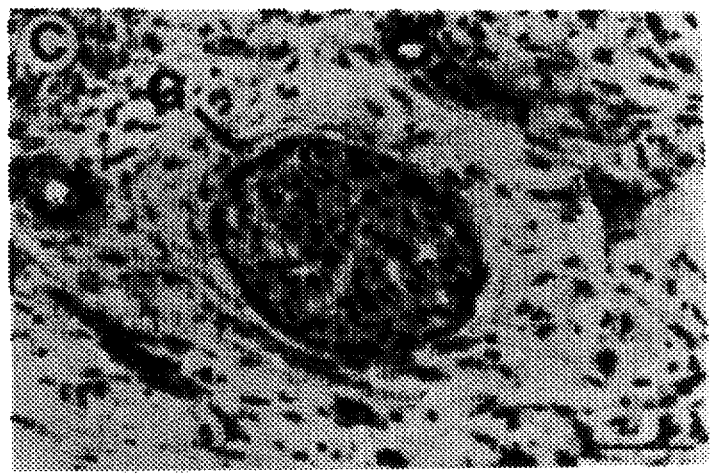
Figure 14D:
Figure 14E:
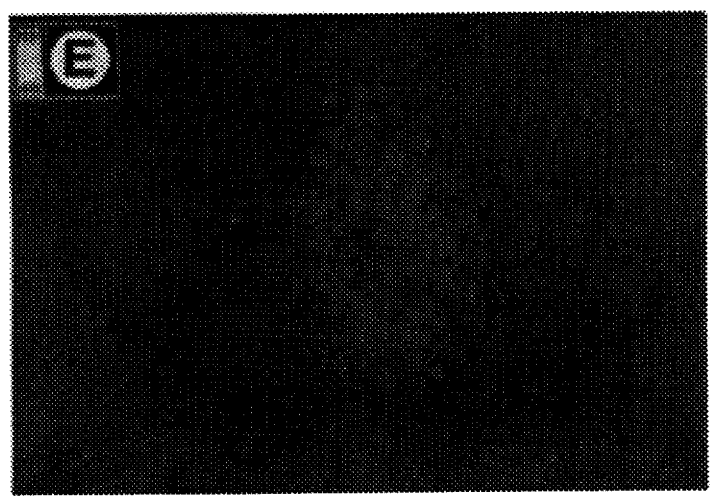

In situ hybridization and immunohistochemistry was used to detect WT1 mRNA expression, as compared with the localization of the WT1 gene product, using the monoclonal antibodies described herein directed against the first alternatively spliced exon of WT1. It has been demonstrated that WT1 is expressed in podocyte cells during menoephric and metanephric development and is present in these cells in adulthood. Expression in male and female gonads is restricted to Sertoli cells, granulosa cells, as well as their precursors. Intracellular localization of the WT1 gene product was carried out with confocal laser microscopy and revealed an exclusively nuclear localization, supporting the proposed role of WT1 as a transcription factor. Also described in Example 5, are the first results to directly demonstrate that WT1 protein is synthesized in Wilms' tumors (FIG. 13).

The expression of WT1 in tissues other than the kidney should focus research on the possible involvement of WT1 in other tumors besides Wilms' tumor. Extrarenal sites of tumors histologically identified as Wilms' tumors have been reported. (Sarode, V. R., et al., *Histopath*. 21:76–78 (1992); Broecker, B. H., et al., *J. Pediat. Surg*. 24:1283–1288 (1989)). Such tumors could possibly arise from extrarenal sites of expression such as the visceral epithelium, which expresses WT1 protein. In one patient with Denys-Drash syndrome, reduction to homozygosity for the mutated WT1 allele was demonstrated in a juvenile granulosa cell tumor which had developed in one case (Pelletier, J., et al., *Cell*, 67:437–447 (1991)). Moreover, the WT1 gene may be expressed in a number of other malignant conditions, such as ovarian cancer (Breuning, W., et al., *Cancer Invest*. 11:393 (1993)), as well as, mesotheliomas (malignant tumors commonly found in workers exposed to asbestos), small cell lung carcinomas, endometrial carcinomas, testicular carcinomas and adult renal carcinomas. Thus, WT1 may contribute to tumorigenesis in other organs which express the protein. The use of the herein described anti-WT1 antibodies will greatly facilitate the search for WT1 expression in other tumors and in the development of diagnostic and therapeutic reagents.

Thus, it is reasonable to expect that the Wilms' tumor gene (i.e., the DNA sequence referred to herein as the Wilms' tumor gene) or a closely-related gene is expressed in other tumor types (e.g., leukemia cells, testicular tumor) and that it is causally associated with those tumor types or serves as a reliable indicator (marker) of such tumor types, although perhaps not directly or solely responsible for formation of a particular type of tumor. Therefore, the methods described herein, and appropriate reagents, such as DNA sequences within the cosmid clones described herein or the Wilms' tumor gene itself or the Wilms' tumor gene product and/or antibodies to the WT1 protein, can be used to identify in other tumor types similar lesions in chromosome 11 band 13. For example, antibodies described herein can be used to identify in a tumor sample (e.g., leukemia cells, testicular tumor) an altered 11p13 sequence resulting in altered gene product, using known techniques and the method described herein.

The polypeptide, or an immunogenic portion thereof, can also be used for therapeutic purposes. For example, it is possible to treat an individual suffering from a cancerous or precancerous condition, preferably the ones being diagnosed by the probes described herein, (i.e., Wilms' tumor) by supplying a therapeutic amount of the Wilms' Tumor suppressor gene product. This can be accomplished by a number of methods known in the art. (Williams, D.A., et al., *Nature* 310:476–480 (1984); Cepko, C. L., et al., *Cell* 37(3) :1053–1062 (1984)). For example, one can use gene transfer techniques to prepare a vector containing a nucleotide sequence corresponding to the Wilms' tumor gene or functional fragment thereof, and use such a vector to transform the malignant cells. The vector is preferably a retroviral vector such as described by Brown and Scott, in *DNA Cloning*, vol III, A Practical Approach, ch. 9, "Retroviral Vectors" CRL Press (1987).

Alternatively, one can use, for example, a Wilms' tumor transformed cell line to produce large amounts of the functional Wilms' tumor gene product which is then isolated and purified so that it is substantially free of pyrogens and endotoxins. The gene product is preferably purified so that is at least about 90% pure, more preferably at least about 95% pure, still more preferably at least about 98% pure. The purified protein is then packaged by standard pharmaceutical procedures so that it can be delivered to the malignant cells, such as by injection, carrier-linked preparations, etc. A therapeutically effective amount of the purified protein is used. The therapeutically effective amount can readily be determined empirically based upon the present disclosure.

The invention will now be illustrated further by the following Examples.

Example 1 Isolation and Characterization of Wilms' TUMOR DNA

Materials and Methods

Cell Culture

Somatic cell hybrids were isolated containing chromosome 11 or translocation chromosomes from patient cell lines DG-85-1436 and GM4613. DG85-1436 is a fibroblast cell line derived from a patient with familial aniridia involving a cytologically balanced translocation of chromosome 11 and 22 [t(11;22) (p13;q12.2)]. Moore, et al., *Hum. Genet.*, 72:297–302 (1986). GM4613 is a fibroblast cell line (Human Genetic Mutant Cell Repository, Camden, N.J.) exhibiting a cytologically balanced translocation involving chromosome 2 and 11 (t(2;11) (p11;p13)) derived from a neonate with Potter syndrome. Potter, *In: Normal and Abnormal Development of the Kidney*, Year Book Medical Publ., Chicago, Ill., pp. 3–79, 83–123 and 259–281 (1972). Somatic cell hybrids were isolated as previously described. Glaser, et al., *Nature*, 321:282–887 (1986). The chromosome 11 haplotype of these hybrids was determined by RFLP analyses with DNA probes on both the short and long arms of chromosome 11. All initial DG hybrids retained the der (11), der (22), and the normal chromosome 11. Cell surface antigen studies revealed that a minor subpopulation of one hybrid, DG-7A-3, possessed only the der (22) chromosome. Two hybrids R19-2C and R19-3B, possessing only the der (22) chromosome were isolated by cell surface antigen selection from the DG-7A-3 population. This was accomplished by selecting for retention of the mer2 surface antigen in 11p15 and selecting against the MIC1 surface antigen centromeric to the translocation in 11p13. In the case of the Potter patient, GM4613 hybrids which retained only the der (11) (BW G2-5), the der 2 (BW A2-5) or the normal 11 chromosome (BW H2-3) were identified by RFLP analysis.

Patient HV has familial aniridia associated with a cytologically balanced translocation involving chromosome 11 and 4 t(4;11) (q22;p13), as described by Simola, et al., *Hum. Genet.*, 63:158–161 (1983). HV human-mouse hybrid R195 contains the der (11) chromosome and HV hybrid LHV-1A5 contains the der (4) chromosome. Hybrids from WAGR patients JH, MH and NW, have been described. Glaser, et al., *Nature*, 321:882–887 (1986). Mouse-human hybrid 15.14 hybrid from Wilms' tumor patient DR with an interstitial deletion of 11p13-p12 (Turleau, et al., *Hum. Genet.*, 67:455–456 (1986)) has been characterized. Genomic DNA from this cell line was kindly provided by Dr. Claudine Junien (INSERM, Paris). Cell line WIT-13 was derived from xenograph cultures of a stage III Wilms' tumor with classical triphasic histology; the tumor arose sporadically in an otherwise healthy two year old female. Lewis, et al., *Genomics*, 3:25–31 (1988).

Isolation of Cosmid Clones

High molecular weight DNA was prepared from the J1-11 hybrid, a Chinese hamster-human somatic cell hybrid possessing only the short arm of human chromosome 11. Kao, et al., *Proc. Natl. Acad. Sci. USA*, 73:193–197 (1976). This DNA was used to construct cosmid libraries in the vectors pJB8 (Ish-Horowitz, et al., *Nucl. Acid. Res.*, 9:2989–2998 1981)) and pWe15 according to the method of Evans and Wahl. Evans, et al., *Methods In Enzym.*, 152:604–610 (1987). DNA was partially digested with the restriction enzyme Mbo I and fragments of 35 to 45 kb were isolated using a 5–25% NaCl gradient. This DNA was ligated to vector DNA and packaged as phage (Gigapack Gold, Stratagene, La Jolla, Calif.) which were used to infect *E. coli* strains 1046 or DH5. Colonies were plated at a low density (1,000 to 2,000 per 150mm plate) on LB-ampicillin plates. Maniatis, et al., *Molecular Cloning: A Laboratory Manual*, Cold Spring Harbor Laboratory, Cold Spring Harbor, N.Y. (1982).

Screening of Genomic Libraries

Standard screening methods were performed, as outlined by Maniatis, et al., (1982) ibid. Replica filters were screened for human positive by hybridization with radiolabeled total human DNA (Gusella, et al., *Proc. Natl. Acad. Sci. USA*, 77:2829–2833 (1988), a cloned human Alu repeat probe (Blur 11) (Jelinik, et al., *Proc. Natl. Acad. Sci. USA*, 77:1398–1402 (1980)) or $Cot_1$ human repeat enriched DNA (Shih, et al., *Cell*, 29:616–619 (1982)). Approximately 0.5% of colonies in the J1-11 library were identified as human positive. Cosmid DNA was isolated from small scale cultures of each of these human positive colonies according to Maniatis, et al., (1982) ibid. The EcoRI restriction pattern of cosmids was analyzed by standard agarose gel electrophoresis.

Mapping of Cosmids

An abbreviated mapping panel of J1 cell hybrids possessing defined segments of human chromosome 11p was used to rapidly identify human cosmids in 11p13. Human cosmids were mapped by preannealing radiolabelled DNA with total sheared human DNA to minimize signal from human repeats (Litt, et al., *Proc. Natl. Acad. Sci. USA*, 82:6206–6210 (1985)) and hybridizing with a nylon (Zetabind, AMF-Cuno) filter of Eco RI digested DNA from J1 cell hybrid.

Isolation of Single Copy Sequences

Single copy sequences were subcloned from cosmids as follows. Cosmids were digested to completion with Sau3A I and the resulting fragments subcloned into the Bam HI polylinker site of the plasmid pUC19. Clones with inserts were gridded on nitrocellulose filters and those with single copy sequences were identified by lack of hybridization to repeat enriched ($Cot_1$) DNA. Random single copy fragments were further tested by hybridizing radiolabelled inserts isolated from low melt agarose gel slices to nitrocellulose filters of human and λphage DNA. Probes J7-18p2 and J9-3p4 were among the single copy sequences identified from these cosmids.

Origin of DNA Probes

Human cosmids J7-18, J8-3 and J10-15 were isolated from the J1-11/pWe15 cosmid library. Four additional cosmids (L156, L159, L155-1, L109) were isolated from a total human pWe15 cosmid library (Stratagene, La Jolla, Calif.) using a 1.8 kb Eco RI fragment of the WT33 cDNA as a probe. The localization of all cosmids to 11p13 was verified by somatic cell mapping. Genomic probes J7-18p2 and J8-3p4 were identified as 0.5 kb and 1.3 kb single copy Eco RI/HindIII fragments in pUC19 from cosmids J7-18 and J8-3, respectively. Phage K13 was isolated from a λdash (Stratagene) library constructed from a BamHI complete digest of Goss-Harris hybrid 3A. The CAT probe is a 0.6 kb PstI-AvaI fragment of the cDNA clone pC24. Bruns, et al., Am. J. Hum. Genet., 36:245 (1984). The FSHB probe is a 1.4 kb PstI insert of pFSH-1.4. Watkins, et al., DNA, 6:205–212 (1987).

Southern Blots

Isolation and digestion of genomic DNA, transfer of DNA to nylon membranes, hybridization of radiolabelled probe, washing of filters, and autoradiography were performed as outlined by Glaser, et al., (1986) ibid. DNA was radiolabeled with $^{32}$p-αdCTP (New England Nuclear) according to the random primer method. Feinberg, et al., *Biochem. Biophys. Res. Comm.*, 111:47–54 (1983).

Screening of cDNA Libraries

Human cDNA libraries of embryonic kidney, adult kidney and pre-B cell origin were screened. Maniatis, et al., (1982) ibid. For screening each library, a total of $10^6$ phage were plated on NZCYM agarose plates and two replicas of each plate were made with nitrocellulose filters. Schleicher and Schull. The replica filters were treated with denaturing solution, neutralizing solution and 2×SCC (1×SCC=0.15M NaCl, 0.015M Na citrate) for 5 minutes each and then baked at 80° C. in a vacuum oven for 2 hours according to Maniatis, et al., (1982) ibid. Replica filters were hybridized with the conserved single copy probe, J8-3p4, or with subfragments of WT cDNAs.

Northern Blots

Total RNA was isolate by a LiCl/urea procedure. Auffray, et al., *Eur. J. Biochem.*, 107:303–314 (1980). cells were harvested, pelleted, resuspended in 3M LiCl/6M urea and homogenized at 4° C. RNA was precipitated, washed in 3M LiCl/6M urea, precipitated and resuspended in TE/-SDS. RNA was extracted in phenolchloroform (2–3×), ethanol precipitated, lyophilized, resuspended, quantitated and stored at −20° C. 10–20 μg of RNA was run on a 1% agarose 37% formaldehyde RNA gel and blotted on Gene Screen Plus (New England Biolabs) membrane. The filters were prehybridized and hybridized at 42° C. for 24 hours in 50% formamide, 5×Denhardts solution, 0.5% SDS (sodium dodecyl sulfate), 10% dextran sulfate, 0.1% pyrophosphate and 100 μg/ml salmon sperm DNA. Blots were hybridized with a conserved genomic probe JS-3p4, cDNA 2-1 (1.5 kb Pst I/Eco RI fragment), a 0.5 kb Sau3a I subclone of cDNA 2-1 Or a 1.8 kb Eco RI fragment of the cDNA WT33. After an 18–36 hour hybridization, blots were washed twice in 2×SSC, 0.1% SDS for 30 minutes at room temperature and one to two times in 1xSSC, 0.1% SDS for 30 minutes at 55°–60° C.

DNA Sequencing

DNA sequencing was done by chain termination, Sanger, et al., *Proc. Natl. Acad, Sci, USA*, 74:5463–5467 (1977) using double stranded DNA templates. Restriction fragments of the WT33 cDNA were subcloned into pUC19 or Bluescript (New England Biolabs). Direct sequencing primers for Bluescript were obtained from New England Biolabs. Additional oligonucleotide primers (synthesized by Research Genetics, Huntsville, Ala.), corresponding to the cDNA were also used for sequencing the cDNAs. The WT33 cDNA was sequenced on both strands (SEQ ID NO: 1). In addition, sequence was confirmed on regions of other cDNAs (WT2, WT4 and WT22). Sequencing reactions were electrophoresed on 6% and 8% polyacrylamide gels, dried and autoradiographed. Using the Fast-P algorithm, Lipman, et al., *Science*, 227:1435–1441 (1985), the predicted amino acid sequence of the cDNA WT33 (SEQ ID NO: 2) was compared with protein sequences stored in the National Biomedical Research Foundation Protein Identification Resource (NBRF/PIR data base).

Results

Isolation and Mapping of Genomic Probes

A cosmid library was constructed from a hybrid cell line, J1-11, in which the short arm of chromosome 11 had been segregated from the remainder of the human genome in a Chinese hamster background. Kao et al., (1976) ibid. A total of 119 cosmid clones containing human DNA sequences were isolated, all of which mapped to the short arm of chromosome 11. To identify clones within the WAGR region, a mapping panel of somatic cell hybrids containing different fragments of human chromosome 11p was used. Glaser, et al., (1989) ibid. Three cosmids, J7-18, J8-3 and J10-15, appeared to map the closest to the region containing the Wilms' tumor gene. The restriction maps of cosmids J8-3 and J10-15 showed substantial overlap. Hence, single copy sequences (J7-18p2 and JS-3p4) were subcloned and identified from cosmids J7-18 and J8-3, respectively.

The fine localization of these single copy DNA sequences within 11p13 was determined by hybridization to a series of somatic cell hybrids derived from patients with translocations and deletions which define specific intervals within the WAGR region. Subclones J7-18p2 and J8-3p4 were hybridized to DNA from hybrid cells derived from an aniridia patient DG. This patient has a cytogenetically balanced 11;22 translocation which bisects band 11p13. The translocation was inherited with aniridia for several generations in his family. Moore, et al., (1986) ibid, and is associated with a small molecular deletion at the breakpoint. Davis, et al., (1988b) ibid.; Gessler, et al., (1989b) ibid. Human DNA sequences homologous to probes J7-18p2 and J8-3p4 were shown to be absent in cell lines R19-2C and R19-3B, which contain only the derivative (der) (22) chromosome. These results, and a normal gene dosage in fibroblast DNA from this patient, place J7-18p2 and J8-3p4 on the centromeric side of the DG translocation breakpoint on chromosome 11. Analogous results were obtained with hybrid cells derived from a second unrelated aniridia patient (HV) also carrying an 11p13 translocation (Table). Accordingly, both cosmids map centromeric to AN2, towards the Wilms' tumor locus.

TABLE

Mapping of 11p13 Probes Using Patient Hybrids

| | | | | Probe | | |
|---|---|---|---|---|---|---|
| Phenotype | Patient | Hybrid | Chromosome 11 Content | J7-18p12 | J8-3p4 | cDNA |
| Aniridia | DG | R19-2C | der (22) | − | − | − |
| | HV | R195 | der (11) | ND | + | + |
| | HV | LHV-1A5 | der (4) | − | − | − |
| Urogenital | BW | H2-3 | N1 (11) | + | + | + |
| | BW | G2-5 | der (11) | − | − | − |
| | BW | A2-5 | der (2) | + | + | + |
| WAGR | JH | c/h | del (11P14.1–p11.2) | − | − | − |
| | NW | F3 | del (11p13) | − | − | − |
| | MJ | A9 | del (11p13) | − | − | − |
| WT (constitutional) | DR | 15.14 | del (11) p13–p12 | + | − | − |
| WT (sporadic) | WiT-13 | D2 & R87 | del (11) pΔS) | + | − | − |
| | WiT-13 | R91 | del (11) pΔL) | − | − | − |

Hybridization of J7-18p2 to DNA from somatic cell hybrids derived from a second patient (BW), an individual with multiple urogenital defects (Potter's syndrome) and a (t(2;11) (p11;p13)) translocation (GM4613; Human Genetic Mutant Cell Repository, Camden, N.J.) was hybridized to J7-18p2 and J8-3p4. The breakpoint of this translocation identifies the site of a potential genetic determinant of genitourinary abnormalities. Porteus, et al., (1987) ibid. Both probes hybridize to cell line A2-5, containing the det (2) chromosome and fail to hybridize to cell line G2-5, containing the der (11) chromosome. Therefore, both are located between the aniridia and Potter translocation breakpoints. Since this interval contains the Wilms' tumor gene, these findings suggest that J7-18p2 and J8-3p4 are close to or within the Wilms' tumor locus.

Analysis of chromosome 11 deletions from WAGR and Wilms' tumor patients (Table) permits more precise localization of these probes in relation to the Wilms' tumor gene. Both J7-18p2 and J8-3p4 are homozygously deleted in three constitution WAGR deletions (patients JH, MJ and NW) tested, consistent with the positioning of these DNA sequences in close proximity to the Wilms' tumor locus.

The position of J7-18p2 and J8-3p4 relative to the Wilms' tumor locus was further investigated by hybridization to DNA from cell lines derived from two Wilms' tumor patients. Patient DR is an individual with a constitutional deletion of 11p12-p13, Couillin, et al., (1988) ibid., terminating between the Wilms' tumor and AN2 loci (Table). J7-18p2 is present in the deleted chromosome 11 of patient DR, whereas J8-3p4 is absent (Table). since catalase is deleted in DR, J7-18p2 must be telomeric to J8-3p4. The distance between these two probes is less than 340 kb. The DR data indicates that the distal boundary of the region which must contain the Wilms' tumor patient WIT-13 has previously been shown. Lewis, et al., (1988) ibid., to carry overlapping 11p13 deletions in tumor tissue, as demonstrated by the homozygous deletion of the anonymous DNA segment D11S87. Since J7-18p2 is present in this chromosome, but JS-3p4 is absent (Table), the $\Delta_s$ (small) deletion chromosome 11 of WIT-13 must have a breakpoint between the two probes. J8-3p4 is homozygously deleted in WIT-13 since it also was found to be absent in the $\Delta_L$ (large) deletion chromosome. The proximal limit to the position of the Wilms' tumor locus is the endpoint of the endpoint of the $\Delta_L$ deletion on WIT-13. The findings that J8-3p4 is homozygously deleted in WiT-13, thus, maps it to the 11p13 region containing the Wilms' tumor locus, an interval which is 345 kb or less based on analysis by pulsed field gel electrophoresis. A map summarizing these findings is shown in FIG. 2.

Isolation of cDNA Clones

Figure 4:
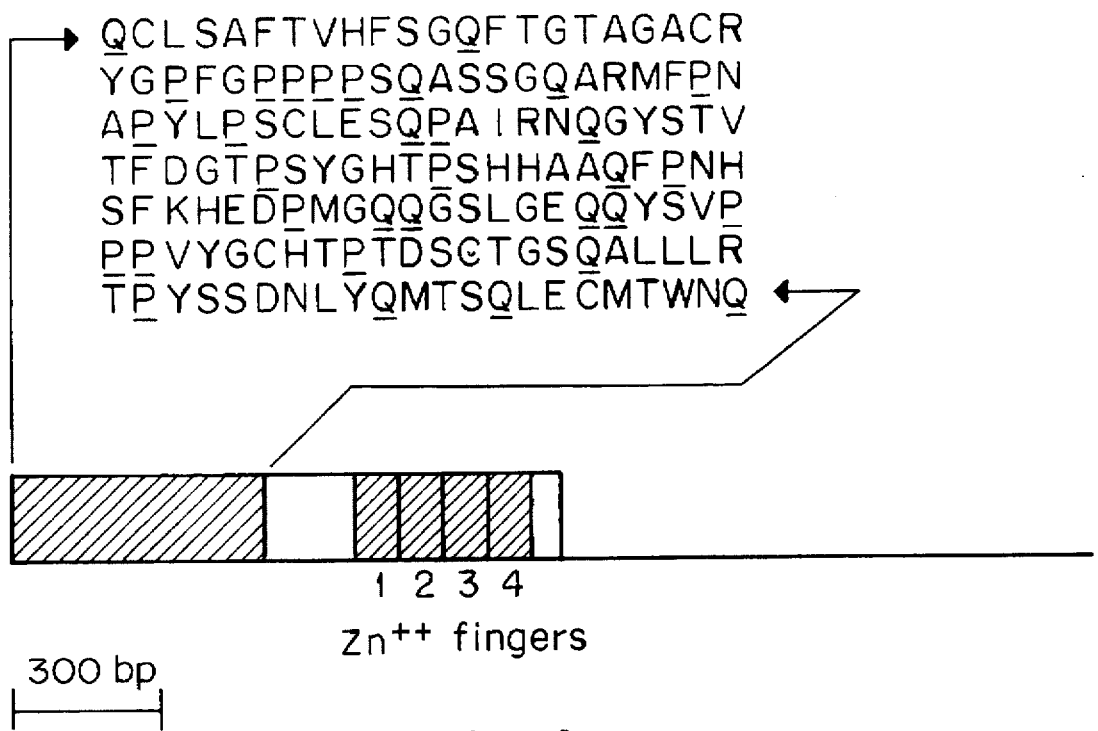
FIG. 4 is a schematic map of the WT33 cDNA; the open reading frame is shown in the boxed region and the deduced amino acid sequence of the proline/glutamine rich region (SEQ ID NO: 5) appears above the shaded open reading frame.

The map position of J8-3p4 indicated that this probe was close to or within the Wilms' tumor locus. Two observations suggested that J8-3p4 contained a portion of a transcription unit. First, strong cross-species hybridization to hamster and mouse DNA genomic sequences was observed in somatic cell hybrids with J8-3p4 (FIGS. 1A and 1B). Cross species conservation is often associated with expressed DNA sequences. Second, JS-3p4 showed hybridization to RNA isolated from baboon kidney ad spleen. J8-3p4 was used as a probe to screen a cDNA library derived from human embryonic kidney (HEK) cells. On the basis of Northern blotting results, a human adult kidney and a human pre B cell library were also screened. Four cDNA clones, two from HEK (WT4, WT2) one from human adult kidney (WT22) and one from a pre B cell line (WT33), were studied in detail. Using another independently isolated conserved genomic DNA clone, λK13, a fifth homologous cDNA clone (WT13) was also isolated from the HEK library. The longest cDNA clone isolated, WT33, is 2313 base pairs in length (FIGS. 3 and 4). The WT33 cDNA extends the furthest in both the 5' and 3' directions. The other four cDNAs share a common internal region of DNA sequence approximately 1000 to 1200 base pairs in length.

Sequence Analysis of the WT33 cDNA

The nucleotide sequence of the WT33 cDNA was determined (SEQ ID NO: 1) and the predicted amino acid sequence (SEQ ID NO: 2) was derived. The sequence of WT33 reveals a continuous open reading frame of 345 amino acids which extends from nucleotide 1 to 1035. A schematic representation of the WT33 cDNA is illustrated in FIG. 3. This open reading frame represents most of the WT33 coding segment, but it does not include the initiator methionine codon. Primer extension experiments suggest that an additional 200 bp are present at the 5' end of the mRNA corresponding to WT33. The transcription pattern of the locus corresponding to WT33. The transcription pattern of the locus corresponding to these cDNAs exhibits some complexity. Experiments utilizing RNA PCR (polymerase chain reaction) indicate variation in mRNA sequence in the 5' segment of the coding region of the mRNA, suggesting alternative splicing patterns among various tissue types.

Of particular interest, nucleotide 670 to 1002 encode four contiguous "zinc finger" domains. The zinc finger motif was first described in Xenopus TF-IIIA which binds to DNA in the internal control region of the 5S genes. Miller, et al., *EMBO. J.*, 4:1609–1614 (1985); Brown, et al., FEBS Lett., 186:271–274 (1985). Subsequently, other nucleic acid recognizing proteins have been reported to contain the zinc finger domain. Klug, et al., TIBS, 12:464 (1987); Evans, et al., *Cell,* 52:1–3 (1988). The zinc finger sequence motif consists of a repeating unit of 29–30 amino acids (Y/F-X-C-$X_{2-4}$-C-$X_3$-F-$X_5$L-$X_2$-H-$X_{3-4}$-H-$X_{6-7}$; where X is any amino acid) which folds into a domain chelating a zinc atom between a pair of cysteines and histidines. Diakun, et al., *Nature,* 324:698–699 (1986); Green, et al., *Proc. Natl. Acad. Sci. USA,* 86:4047–4051 (1989). All four zinc fingers encoded by WT33 (FIGS. 4 and 5) fit the consensus sequence for zinc fingers. The H/C link between zinc fingers, typified by the amino acid sequence TGE-R/K-P-F/Y-X. Suh, et al., *Cell,* 47:1025–1032 (1986), is also conserved in the deduced amino acid sequence of WT33.

Example 2 Bacterial Expression of Wilms' Tumor Gene Product

A plasmid encoding a glutathione S-transferase (GST) Wilms' Tumor fusion protein (GST-WT) containing amino acid residues 95–295 (numbers refer to FIG. 3 (SEQ ID NO: 2)) of the Wilms' Tumor protein was generated by insertion of a fragment of the Wilms' tumor cDNA into the bacterial expression vector pGEX-3X (Pharmacia). The plasmid WT33 was digested with Bam H1 and rendered blunt with Klenow followed by restriction with Rsr II. The resulting fragment was ligated to a DNA linker (McGill University Dept. of Biochemistry) containing a stop codon and subcloned into the blunted Bam H1 site of pGEX-3X. The resulting plasmid pGEX/h W.T. was introduced into *E. coli* strain NB42. Growth induction and isolation of the fusion protein was performed according to the manufacturers instructions. Expression was analyzed by SDS-PAGE.

This plasmid is capable of expressing a ~50 kDa protein. This protein is soluble and binds efficiently to Glutathione sepharose (Pharmacia #17-0756-01). In contrast to the GST portion alone, the GST-WT protein is insoluble and can not be purified by glutathione sepharose affinity chromatography.

A plasmid encoding a glutathione S-transferase (GST) Wilms' tumor fusion protein containing amino acid residues 182–404 (numbers refer to FIG. 9A and 9B (SEQ ID NO: 4) of Wilms' tumor protein was generated, expressed and characterized as described above for the WT33 fusion protein.

Example 3 Characterization of Polyclonal Antibodies

Polyclonal antibodies were prepared by immunization of rabbits using WT1-GST fusion protein, obtained as described in Example 2. The immunization protocol followed standard laboratory procedure. One hundred micrograms of fusion protein was mixed with Freund's complete adjuvant and injected subcutaneously into New Zealand White Rabbits. Each rabbit was injected subcutaneously, in 10 different sites, with 100 ul dose per site (containing 10 ug of recombinant protein). Four rabbits in total were immunized by this procedure. Boosts were performed at 3 week intervals following the initial immunization inject. For boosts, 100 ug of antigen was mixed with incomplete Freund's adjuvant. Test bleeds were taken 14 days after the second boost. 5mls of serum was isolated from the test bleeds and western blots performed to establish immunoreactivity of the serum.

Serum obtained from one immunized rabbit was tested for reactivity of the anti-WT1 antibody by immunoprecipitation of the WT1 polypeptide using the anti-WT1 polyclonal antibody as follows. COS-1 cells were transfected with CMV-based expression vectors expressing the four WT1 isoforms (Pelletier, J., et al., Genes Dev., 5:1345-1356 (1991)). Two days after transfection, the cells were labelled with $^{35}$S-methionine (~100 µCi/ml) and cell extracts were prepared by lysis in RIPA buffer (150 mM NaCl, 1% NP-40, 0.5% sodium deoxycholate, 0.1% SDS, 50 mM Tris-HCl (pH8.0), 0.5 mM PMSF). Half of the cell extract was incubated with 3 µl of polyclonal and WT1 antibody. After incubation at 4° C. overnight, 80 µl of 50% slurry of Protein G agarose (Gibco/BRL) was added to the reaction mixture and allowed to rotate end-over-end at 22° C. for one hour. After washing 4 times with PBS, samples were prepared for electrophoresis and analyzed by SDS/PAGE and autoradiography (FIG. 11). The five lanes demonstrated the following: lane 1, control COS-1 extracts without WT1 protein; lane 2, COS-1 cells expressing the [-/-] WT1 isoform; lane 3, COS-1 cells expressing [-/+] WT1 isoform; lane 4, COS-1 cells expressing [+/-] WT1 isoform; lane 5, COS-1 cells expressing [+/+] WT1 isoform. The different spliced WT1 protein products are clearly visible on the autoradiography.

Example 4 Preparation and Characterization of Monoclonal Antibodies

Peptides containing the sequence VAAGSSSSVKW-TEGQSN (+Δ1) (SEQ ID NO: 7) or LGATLKGHST-GYESD (-Δ1) (SEQ ID NO: 8) were synthesized and used for immunization. Peptides were coupled to malamide activated keyhold limpet hemocyanin according to the manufacturer's instructions (Pierce). Monoclonal antibodies were generated as follows. Spleen cells of BalB/c mice immunized with conjugated peptides were fused to SP2/0 myeloma cells according to the procedure of (Batin, R. and Lemieux, R. J., J. Immunol. Methods 116:245-249 (1989). Antibody-secreting hybridomas were screened and selected by a standard antigen-coated will ELISA. Hybridomas that showed high reactivity on ELISA were cloned by limiting dilution. Six cloned monoclonals were then purified in protein G agarose as specified by the supplier (Gibco/BRL).

For preparation of protein for Western blot analysis, COS-1 cells were transfected as previously described with CMV-based expression vectors which produced WT1 isoforms (+Δ1) (SEQ ID NO: 7) or lacking (-Δ1) (SEQ ID NO: 8) the first alternative splice site. Total cell proteins were prepared 2 days after transfection as follows: Cells (10 cm$^2$ dish containing approximately, 10$^6$ cells) were washed 2× in PBS, lysed in 0.5 ml of 2% sds/56 mM Tris, pH7.5. The mixture was heated in a boiling water bath for 10 minutes. DNA was sheared by passage through a 25-gauge needle 15 times and centrifuged at 10,000×g for 10 minutes. Forty microliters of supernatant were electrophoresed on a SDS/10% polyacrylamide gel, the gel was transferred to nitrocellulose, and subjected to immunoblot analysis. The WT1 (-/-) isoform (lanes 2, 4, 6, 8) or the WT1 (+/+) isoform (lanes 1, 3, 5, 7). The blot was incubated with different anti-WT1 monoclonal antibodies (diluted 1:500) as indicated in FIG. 12. The protein was visualized using the ECL Western blot detection kit (Amersham). The WT1 (SEQ ID NO: 4) protein is indicated in FIG. 12 with an arrowhead. None of the monoclonal antibodies reacted with cellular proteins form COS-1 cells, as judged by the absence of additional bands in lanes 1 to 8.

Example 5 Detection of the Wilm's Tumor Protein in Wilm's Tumor Tissue

Protein extracts from frozen Wilms' tumors were prepared as follows. A small piece of tumor tissue (~0.5 cm$^3$) was ground to powder under liquid nitrogen with a pestle and mortar. The powder was homogenized into 5 mls of 2% SDS/50 mM Tris-HCl (pH8.0). The mixture was boiled for 5 mins., the DNA was sheared through an 18 gauge needle, and centrifuged at 10,000×g for 10 min. The supernatant was taken, aliquoted and stored at -70° C. Samples of WT tissue were obtained from Dr. Tom Shows.

Protein extracts from frozen Wilms' tumors were diluted in buffer appropriate for SDS/PAGE. The protein extracts were resolved by SDS/PAGE and processed for Western blotting as described in Example 4. The Western blot was incubated with the polyclonal anti-WT1 antibody (1:200) and stained for alkaline phosphatase color reaction using the protocols described by Promega Biotech. The presence of a 52–54 kDa set of proteins (which is the predicted molecular weight of the WT1 isoforms) are visible as two bands in all tumor samples, as well as normal kidney (FIG. 14).

In situ Hybridization and Immunofluorescence

The techniques employed for in situ hybridization were as previously described in (Mundlos, S., et al., Matrix 11:339-346 (1990). The tissue was fixed in 4% buffered formalin, immersed in 0.5 M sucrose and snap frozen in liquid nitrogen. Frozen sections were mounted on triethoxyethanolamine treated microscope slides. The slides were immersed in 4% paraformaldehyde in PBS for 15 minutes, followed by digestion with pronase (Boehringer) at 0.3 mg/ml for 8 minutes at room temperature, fixation in paraformaldehyde for 10 minutes, and dehydration in a graded series of ethanol steps. Probes were diluted to a specific activity of 10$^5$ dmp/µl in hybridization buffer (50% formamide, 10% dextran sulfate, 0.3 M NaCl, 10 mM Tris, pH 7, 10 mM NaHPO$_4$, pH 5, 5.5 mM EDTA, 0.02% Denhardts', and tRNA (0.5 mg/ml). Hybridization was performed overnight at 42° C. The slides were washed in 50% formamide/2×SSC at 45° C. for 2 hours followed by incubation with 20 µg/ml RNAse A (Sigma, München, F.R.G.) for 15 minutes and again washed three times in 2×SSC for 15 minutes at room temperature. After dehydration, slides were dipped in Kodak NTB-2 photoemulsion diluted 1:1 with water and air dried. Exposure time varied from 10–20 days. The exposed slides were developed, fixed, stained, and examined using the Zeiss system for epipolarization.

Immunofluorescence was carried out using unfixed, snap frozen material. Frozen sections were cut and mounted on triethoxyethanolamine treated slides. Tissue was fixed for 1 hour in Methanol/EDTA (0.02%), air dried, and hydrated in PBS, pH 7.4. The first antibody was applied at a dilution of 1:100 to 1:300 and incubated at room temperature in a moist chamber for 1 hour. A CY3-coupled anti-mouse (Caco; dilution 1:200) was used for detection. Parallel experiments with positive and negative controls (minus first antibody) were always performed. The slides were examined on a Zeiss fluorescence microscope. Investigation of the intracellular localization of the WT1-protein was performed on a Zeiss laser scanning microcsscope.

Immunofluorescence showing nuclear staining in (FIG. 14B) blastema and (FIG. 14D) glomeruloid structures. Bright light images show blastema (FIG. 14A) and glomeruloid structures (FIG. 14C), confocal microscopy phase contrast overlay (FIG. 14E) (FIGS. 14A–14E).

Equivalents

Those skilled in the art will recognize or be able to ascertain, using no more than routine experimentation, many equivalents to the specific embodiments of the invention described herein. Such equivalents are intended to be encompassed within the scope of this invention.

|---|---|---|---|---|---|---|---|---|---|---|---|---|---|---|

The invention claimed is:

1. An isolated polypeptide encoded by Wilms' tumor DNA, said DNA comprising the nucleic acid sequence SEQ ID NO: 1.

2. An isolated polypeptide comprising the amino acid sequence SEQ ID NO: 2 or SEQ ID NO: 5.

3. An isolated polypeptide encoded by the 11p13 Wilms' tumor gene, said polypeptide comprising about 345 consecutive amino acid residues of SEQ ID NO:2.

4. An isolated polypeptide comprising SEQ ID NO: 2 or SEQ ID NO: 5, detectable by an antibody specific for gene product, said gene product encoded by a nucleic acid sequence comprising SEQ ID NO: 1.

5. An isolated polypeptide comprising SEQ ID NO: 2 or SEQ ID NO: 5, detectable by an antibody specific for the 11p13 Wilms' tumor gene product encoded by SEQ ID NO: 1.

* * * * *